(12) United States Patent
Kaltenbach et al.

(10) Patent No.: US 6,927,224 B2
(45) Date of Patent: Aug. 9, 2005

(54) SELECTIVE ESTROGEN RECEPTOR MODULATORS

(75) Inventors: Robert F. Kaltenbach, Wilmington, DE (US); Simon P. Robinson, Stow, MA (US); George L. Trainor, Wilmington, DE (US)

(73) Assignee: Bristol Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/216,253

(22) Filed: Aug. 9, 2002

(65) Prior Publication Data

US 2003/0105148 A1 Jun. 5, 2003

Related U.S. Application Data

(60) Provisional application No. 60/311,466, filed on Aug. 11, 2001.

(51) Int. Cl.$^7$ .................. A61K 31/24; C07C 311/00
(52) U.S. Cl. .................. 514/331; 514/367; 514/539; 514/602; 514/603; 514/604; 514/605; 514/445; 549/65; 546/234; 548/167; 560/12; 564/89; 564/97; 564/86; 564/88; 564/91; 564/87; 564/99; 562/98
(58) Field of Search ................. 514/605, 331, 514/367, 539, 602, 603, 604, 445; 562/98; 549/65; 546/234; 548/167; 560/12; 564/89, 97, 86, 88, 91, 87, 99

(56) References Cited

U.S. PATENT DOCUMENTS 5,681,835 A 10/1997 Willson
6,005,003 A 12/1999 Nique

FOREIGN PATENT DOCUMENTS

| WO | WO 99/08682 | 2/1999 |
| WO | WO 01/26651 | 4/2001 |
| WO | WO 01/77055 | 10/2001 |
| WO | WO 01/77057 | 10/2001 |

OTHER PUBLICATIONS

Willson, T.M. et al., "3-[4-(1, 2-Diphenylbut-1-enyl)phenyl]acrylic Acid: A Non-Steroidal Estrogen with Functional Selectivity for Bone over Uterus in Rats", J. Med. Chem., vol. 37, pp. 1550-1552 (1994).
Weatherman, R.V. et al., "Differential SERM activation of the estrogen receptors (ERα and ERβ) at AP-1 sites", Chemistry & Biology, vol. 8, pp. 427-436 (2001).
Database CAPLUS [Online] Chemical Abstracts Service, Columbus, Ohio, U.S., Database accession No. 121:34956 XP0022222761 *RNs: 155701-59-0, 155701-64-4, 155701-70-5, 155701-71-6* abstract (1994).
Eaker, E.D. et al., "Cardiovascular Disease in Women", Circulation, vol. 88, No. 4, Part 1, pp. 1999-2009 (1993).
Evans, R.M., "The Steroid and Thyroid Hormone Receptor Superfamily", Science, vol. 240, pp. 889-895 (1988).
Jordan, V.C. et al., "Endocrine Pharmacology of Antiestrogens as Antitumor Agents", Endocrine Reviews, vol. 11, No. 4, pp. 578-610 (1990).
Kedar, R.P. et al., "Effects of tamoxifen on uterus and ovaries of postmenopausal women in a randomised breast cancer prevention trial", Lancet, vol. 343, pp. 1318-1321 (1994).
Love, R.R. et al., "Effects of Tamoxifen on Bone Mineral Density in Postmenopausal Women with Breast Cancer", The New England Journal of Medicine, vol. 326, No. 13, pp. 852-856 (1992).
Love, R.R. et al., "Effects of Tamoxifen on Cardiovascular Risk Factors in Postmenopausal Women", Annals of Internal Medicine, vol. 115, pp. 860-864 (1991).
McCague, R. et al., "Synthesis and Estrogen Receptor Binding of 6,7-Dihydro-8-phenyl-9-[4-[2-(dimethylamino)ethoxy]phenyl]-5H-benzocycloheptene, a Nonisomerizable Analogue of Tamoxifen. X-ray Crystallographic Studies", J. Med. Chem. vol. 29, pp. 2053-2059 (1986).
McDonnell, D.P. et al., "Analysis of Estrogen Receptor Function in Vitro Reveals Three Distinct Classes of Antiestrogens", Molecular Endocrinology, vol. 9, No. 6, pp. 659-669 (1995).
Parker, M.G., "Action of 'pure' antiestrogens in inhibiting estrogen receptor action", Breast Cancer Research and Treatment, vol. 26, pp. 131-137 (1993).
Tasset, D. et al., "Distinct Classes of Transcriptional Activating Domains Function by Different Mechanisms", Cell, vol. 62, pp. 1177-1187 (1990).
Tonetti, D.A. et al., "Possible mechanisms in the emergence of tamoxifen-resistant breast cancer", Anti-Cancer Drugs, vol. 6, pp. 498-507 (1995).
Tora, L. et al., "The Human Estrogen Receptor Has Two Independent Nonacidic Transcriptional Activation Functions", Cell, vol. 59, pp. 477-487 (1989).
Tzukerman, M.T. et al., "Human Estrogen Receptor Transactivational Capacity is Determined by both Cellular and Promoter Context and Mediated by Two Functionally Distinct Intramolecular Regions", Molecular Endocrinology, vol. 8, No. 1, pp. 21-30 (1994).

(Continued)

*Primary Examiner*—Laura L. Stockton
(74) *Attorney, Agent, or Firm*—Jacqueline M. Cohen; Elliott Korsen

(57) ABSTRACT

The present invention provides, inter alia, triphenylethylene derivatives, such as, 3-{4-[6-(3-Methoxy-phenyl)-8,9-dihydro-7H-benzocyclohepten-5-yl]-phenyl}-acrylic acid, as selective estrogen receptor modulators. Also provided are methods for the treatment and/or prevention of estrogen stimulated diseases in mammals including breast, uterine, ovarian, prostrate and colon cancer, osteoporosis, cardiovascular disease, and benign proliferative disorders, as well as pharmaceutical compositions of the compounds of the present invention.

9 Claims, No Drawings

OTHER PUBLICATIONS

Wagner, B.L. et al., "16α–substituted analogs of the anti-progestin RU486 induce a unique conformation in the human progesterone receptor resulting in mixed agonist activity", Proc. Natl. Acad. Sci. USA, vol. 93, pp. 8739–8744 (1996).

Beekman, J.M. et al., "Transcriptional Activation by the Estrogen Receptor Requires a Conformational Change in the Ligand Binding Domain", Molecular Endocrinology, vol. 7, No. 10, pp. 1266–1274 (1993).

Black, L.J. et al., "Raloxifene (LY139481 HCl) Prevents Bone Loss and Reduces Serum Cholesterol without Causing Uterine Hypertrophy in Ovariectomized Rats", J. Clin. Invest., vol. 93, pp. 63–69 (1994).

Chow, J. et al., "Estrogen Maintains Trabecular Bone Volume in Rats Not Only by Suppression of Bone Resorption but Also by Stimulation of Bone Formation", J. Clin. Invest., vol. 89, pp. 74–78 (1992).

Scanlan, Thomas S., "Differential SERM activation of the estrogen receptors (ERα and ERβ) at AP–1 sites", Chemistry & Biology, vol. 8, No. 5, pp. 427–436 (2001) (XP002220838).

PCT International Search Report mailed Feb. 26, 2003.

SELECTIVE ESTROGEN RECEPTOR MODULATORS

CROSS-REFERENCE TO RELATED APPLICATIONS

This application claims the priority benefit of U.S. Provisional Application No. 60/311,466, filed Aug. 11, 2001, the disclosure of which is incorporated herein by reference in its entirety.

FIELD OF THE INVENTION

This invention pertains to triphenylethylene derivatives, such as, 3-{4-[6-(3-Methoxy-phenyl)-8,9-dihydro-7H-benzocyclohepten-5-yl]-phenyl}-acrylic acid, as selective estrogen receptor modulators. This invention also provides methods for the treatment and/or prevention of estrogen stimulated diseases in mammals including breast, uterine, ovarian, prostrate and colon cancer, osteoporosis, cardiovascular disease, and benign proliferative disorders, as well as pharmaceutical compositions of the compounds of the present invention.

BACKGROUND OF THE INVENTION

Approximately 180,000 women are diagnosed with breast cancer each year in the United States. Most of these women are cured of their disease by surgery and local radiotherapy. However, nearly 60,000 women go on to develop metastatic breast cancer each year, and 45,000 of these patients eventually die from their malignancies. While metastatic breast cancer is rarely curable, it is treatable with modern pharmaceuticals that prolong patient survival and reduce the morbidity associated with metastatic lesions. Foremost among these therapies are hormonal manipulations that include selective estrogen receptor modifiers (SERMs). SERMs are small ligands of the estrogen receptor that are capable of inducing a wide variety of conformational changes in the receptor and thereby eliciting a variety of distinct biological profiles. SERMs not only affect the growth of breast cancer tissue but also influence other physiological processes. The most widely used SERM in breast cancer is tamoxifen, which is a partial estrogen receptor agonist/antagonist that produces objective responses in approximately 50% of the patients. Unfortunately, 100% of patients who take tamoxifen eventually relapse with tamoxifen-resistant tumors. Approximately 50% of the patients that fail tamoxifen treatment will respond to a subsequent hormonal manipulation therapy such as castration, aromatase inhibitors, or other SERMs. The second line therapies for hormonal manipulation therapy of metastatic breast cancer represent a substantial unmet need because no single agent has become the treatment of choice for patients who fail tamoxifen therapy. The ideal agent would be a medication that induces regression of metastatic breast cancer lesions in women who have previously responded to tamixofen therapy. The present invention is directed to novel, highly soluble salt forms of the compound 3-[4[(1,2-diphenyl-but-1-enyl)-phenyl]-acrylic acid, which is described in U.S. Pat. No. 5,681,835, the contents of which are herein incorporated by reference in their entirety.

SERMs modulate the proliferation of uterine tissue, skeletal bone density, and cardiovascular health, including plasma cholesterol levels. In general, estrogen stimulates breast and endometrial tissue proliferation, enhances bone density, and lowers plasma cholesterol. Many SERMs are bifunctional in that they antagonize some of these functions while stimulating others. For example, tamoxifen, which is a partial agonist/antagonist at the estrogen receptor inhibits estrogen-induced breast cancer cell proliferation but stimulates endometrial tissue growth and prevents bone loss. Estrogens are an important class of steroidal hormones that stimulate the development and maintenance of fundamental sexual characteristics in humans. In the past, estrogens have been found useful in the treatment of certain medical conditions and diseases. For example estradiol, a steroid hormone produced by the ovary, is useful in the treatment of osteoporosis, cardiovascular disease, premenstrual syndrome, vasomotor symptoms associated with menopause, atrophic vaginitis, Kraurosis vulvae, female hypogonadism, primary ovarian failure, excessive hair growth and prostatic cancer.

Hormone replacement therapy (HRT) with estrogen has been determined to be a clinically effective treatment for osteoporosis in post-menopausal women. However, less than 15% of eligible women are currently prescribed HRT despite clinical trials that have demonstrated a 50% reduction in hip fractures and a 30% reduction in cardiovascular disease. Non-compliance arises from patient and physician concerns over the two fold increased risk of endometrial cancer observed with HRT employing estrogen alone as well as the association between estrogen therapy and breast cancer. Although unproven in the clinic, this suspected risk for breast cancer has led to HRT being contraindicated in a significant percentage of post-menopausal women. Co-therapy with progestins has been shown to protect the uterus against cancer while maintaining the osteoprotective effects of the estrogen, however the progestin introduces other side effects such as withdrawal bleeding, breast pain and mood swings.

In light of the more serious side effects associated with estrogen therapy, including myocardial infarction, thromboembolism, cerebrovascular disease, and endometrial carcinoma, a significant amount of research has been carried out to identify effective nonsteroidal estrogen and antiestrogenic compounds. In general, such compounds may be characterized as both estrogenic and antiestrogenic because, while they all bind to the estrogen receptor, they may induce an estrogenic or antiestrogenic effect depending upon the location of the receptor. In the past, it has been postulated that the binding of various nonsteroidal estrogen and antiestrogenic compounds to the estrogen receptor was due to the presence of a common pharmacophore (shown below in Scheme A), which was recurrent in the chemical structures of these compounds.

Scheme A

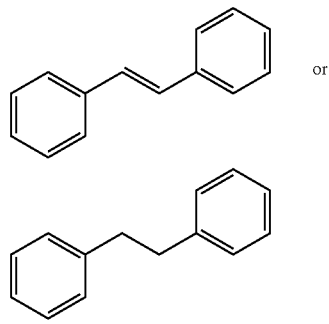

This pharmacophore later became the structural backbone around which nonsteroidal estrogen and antiestrogenic compounds were constructed. Its presence in the constructs of various compounds such as hexestrol, tamoxifen, chroman, triphenylethylene, DES, clomiphene, centchroman, nafoxidene, trioxifene, toremifene, zindoxifene, raloxifene, droloxifene, DABP, TAT-59 and other structurally related compounds has become accepted in the art as the molecular key to estrogen receptor binding specificity.

Estrogen has also been shown to function as a mitogen in estrogen-receptor (ER) positive breast cancer cells. Thus, treatment regiments which include antiestrogens, synthetic compounds which oppose the actions of estrogen have been effective clinically in halting or delaying the progression of the disease (Jordan and Murphy, Endocrine Reviews 11:578–610 1990); Parker, Breast Cancer Res. Treat. 26:131–137 (1993)). The availability of these synthetic ER modulators and subsequent dissection of their mechanism(s) of action have provided useful insights into ER action.

The human estrogen receptor (ER) is a member of the nuclear receptor superfamily of transcription factors (Evans, Science 240:889–895 (1988)). In the absence of hormone, it resides in the nucleus of target cells in a transcriptionally inactive state. Upon binding ligand, ER undergoes a conformational change initiating a cascade of events leading ultimately to its association with specific regulatory regions within target genes (O'Malley et al., Hormone Research 47:1–26 (1991)). The ensuing effect on transcription is influenced by the cell and promoter context of the DNA-bound receptor (Tora et al. Cell 59:471–487 (1989) (Tasset et al., Cell 62:1177–1181 (1990); McDonnell et all Mol. Endocrinol. 9:659–669 (1995); Tzukerman et al. Mol. Endocrinol. 8:21–30 (1994)). It is in this manner that the physiological ER-agonist, extradiol, exerts its biological activity in the reproductive, skeletal and cardiovascular systems (Clark and Peck, Female Sex Steroids:Receptors and Function (eds) Monographs Springer-Verlag, New York (1979); Chow et al., J. Clin. Invest.89:74–78 (1992); Eaker et al. Circulation 88:1999–2009 (1993)).

One of the most studied compounds in this regard is tamoxifen (TAM), (Z)1,2-diphenyl-1-[4-[2-(dimethylamino) ethoxy]phenyl]-1-butene, (Jordan and Murphy, Endocrine Reviews 11:578–610 (1990)), which is a triphenylethylene derivative. Tamoxifen functions as an antagonist in most ER-positive tumors of the breast and ovum, but displays a paradoxical agonist activity in bone and the cardiovascular system and partial agonist activity in the uterus (Kedar et al. Lancet 343:1318–1321 (1994); Love et al., New Engl. J. Med. 326:852–856 (1992); Love et al., Ann. Intern. Med. 115:860–864 (1991)). Thus, the agonist/antagonist activity of the ER-tamoxifen complex is influenced by cell context. This important observation is in apparent contradiction to longstanding models that hold that ER only exists in the cell in an active or an inactive state (Clark and Peck, Female Sex Steroids:Receptors and Functions (eds) Monographs on Endocrinology, Springer-Verlag, New York (1979)). It indicates instead that different ligands acting through the same receptor can manifest different biologies in different cells. Definition of the mechanism of this selectivity is likely to advance the understanding of processes such as tamoxifen resistance, observed in most ER-containing breast cancers, where abnormalities in ER-signaling are implicated (Tonetti and Jordan, Anti-Cancer Drugs 6:498–507 (1995)).

Tamoxifen, as well as a structurally similar compound known as raloxifene have been developed for the treatment and/or prevention of osteoporosis, cardiovascular disease and breast cancer in addition to the treatment and/or prevention of a variety of other disease states. Both compounds have been shown to exhibit an osteoprotective effect on bone mineral density combined with a positive effect on plasma cholesterol levels and a greatly reduced incidence of breast and uterine cancer. Unfortunately, tamoxifen and raloxifene both have unacceptable levels of life-threatening side effects such as endometrial cancer and hepatocellular carcinoma.

The likely mechanism for the cell selective agonist/antagonist activity of tamoxifen has been determined using an in vitro approach (Tora et al., Cell 59:477487 (1989); Tasset et al., Cell 62:1177–1187 (1990); McDonnell et al., Mol. Endocrinol. 9:659–669 (1995); Tzukerman et al., Mol. Endocrinol. 8:21–30 (1994)). Importantly, it has been shown that tamoxifen induces a conformational change within ER which is distinct from that induced by estradiol (McDonnell et al., Mol. Endocrinol. 9:659–669 (1995); (Beekman et al., Molecular Endocrinology 7:1266–1274 (1993)). Furthermore, determination of the sequences within ER required for transcriptional activity indicate how these specific ligand-receptor complexes are differentially recognized by the cellular transcriptional machinery. Specifically, it has been shown that ER contains two activation domains, AF-1 (Activation Function-1) and AF-2, which permit its interaction with the transcription apparatus. The relative contribution of these AFs to overall ER efficacy differs from cell to cell (Tora et al., Cell 59:477–487 (1989); McDonnell et al., Mol. Endocrinol. 9@65-9-669 (1995); Tzukerman et al., Mol. Endocrinol. 8:21–30 (1994)). Estradiol was determined to function as both an AF-1 and an AF-2 agonist, in that it exhibited maximal activity regardless of which AF was dominant in a given cellular environment. Tamoxifen, on the other hand, functions as an AF-2 antagonist, inhibiting ER activity in cells where AF-2 is required or is the dominant activator (Tora et al., Cell 59:477–487 (1989); McDonnell et al., Mol. Endocrinol. 9:659–669 (1995); Tzukerman et al., Mol. Endocrinol. 8:21–30 (1994)). Conversely, tamoxifen functions as an agonist when AF-1 alone is required (McDonnell et al., Mol. Endocrinol. 9:659–669 (1995); Tzukerman et al., Mol. Endocrinol. 8:21–30 (1994)). Subsequently, based on their relative AF-1/AF-2 activity, four mechanistically distinct groups of ER-modulators were defined; full agonists (i.e. estradiol), two distinct classes of partial agonists, represented by tamoxifen and raloxifene, and the pure antagonists, of which ICI182,780 is a representative member (McDonnell et al., Mol. Endocrinol. 9:659–669 (1995); Tzukerman et al., Mol. Endocrinol. 8:21–30 (1994)). These results provide a mechanistic explanation for the observed differences in the biological activities of some ER-modulators and indicate that the mechanism by which ER operates in different tissues is not identical.

Interestingly, the agonist activity exhibited by ER-modulators, such as estrogen and tamoxifen, in these in vitro systems reflects their activity in the reproductive tracts of whole animals. This correlation does not extend to bone, however, where estradiol, tamoxifen and raloxifene, which display different degrees of AF-1/AF-2 agonist activity, all effectively protect against bone loss in the ovariectomized rat model. Thus, with the exception of the steroidal pure antiestrogens (ie, ICI182,780), all known classes of ER modulators appear to protect against bone loss in humans and relevant animal models, while they display different degrees of estrogenic activity in other tissues (Chow et al., J. Clin. Invest. 89:74–78 (1992); Love et al., New Engl. J. Med. 326:852–856 (1992); Draper et al., Biochemical Markers of Bone and Lipid Metabolism in Healthy Postmenopausal Women. In C. Christiansen and B. Biis (eds) Proceedings 1993. Fourth International Symposium on Osteoporosis and Consensus Development Conference, Handelstrykkeriet, Aalborg; Wagner et al., Proc. Natl. Acad. Sci. USA 93:8739–8744 (1996); Black et al., J. Clin. Invest 93:63–69 (1994)).

A series of non-steroidal compounds that retain beneficial characteristics such as osteoprotective activity while minimizing any undesirable side effects would be most advantageous. While it is presently accepted that the pharmacophore backbone mentioned above is responsible for estrogen receptor binding specificity, it has now been discovered that certain novel estrogen binding ligands can be constructed as described herein which incorporate particular moieties onto such pharmacophore-based compounds, thereby maximizing beneficial characteristics such as osteoprotective function while minimizing undesirable characteristics such as an increased risk of cancer.

The present invention provides selective estrogen receptor modulators, which retain beneficial characteristics while minimizing undesirable side effects such as increased risk of cancer.

SUMMARY OF THE INVENTION

The present invention describes compounds represented by Formula (I):

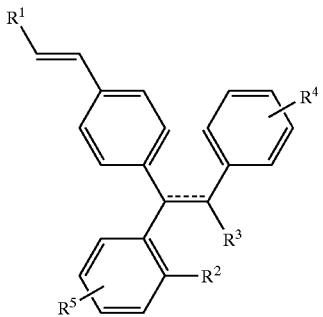

(I)

wherein $R^1$–$R^5$ are defined below.

The present invention is also directed to pharmaceutical compositions comprising one or more compounds of Formula (I).

In addition, the present invention is directed to methods for the treatment and/or prevention of estrogen stimulated diseases including breast, uterine, ovarian, prostate and colon cancer, osteoporosis, cardiovascular disease, and benign proliferative disorders, comprising: administering to a host in need of such treatment a therapeutically effective amount of a compound of Formula (I).

The present invention further provides methods of modulating the estrogen receptor in a patient comprising the step of administering to the patient a therapeutically effective amount of a compound of Formula (I).

The present invention further provides pharmaceutical compositions including compounds of Formula (I) and a pharmaceutically acceptable carrier.

DETAILED DESCRIPTION OF THE INVENTION

This invention pertains to compounds of Formula (I) as selective estrogen receptor modulators:

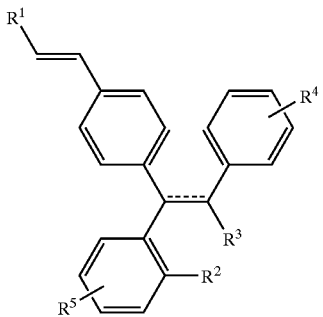

(I)

wherein
$R^1$ is selected from the group consisting of

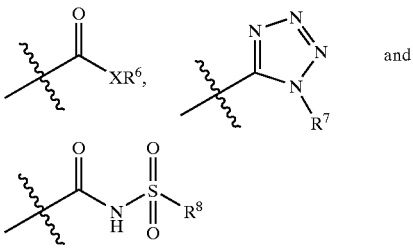

$R^2$ is selected from the group consisting of H, $C_{1-8}$ alkyl and halo;
$R^3$ is selected from the group consisting of H, $C_{1-8}$ alkyl, $C_{1-8}$ alkylenyl, halo, or CN;
alternatively $R^2$ and $R^3$, together with the atoms to which they are attached, form a six- or seven-membered ring structure where one or more of the atoms forming the ring may be oxygen;
$R^4$ is selected from the group consisting of H, OH, $C_{1-8}$ alkyl, $OC_{1-8}$ alkyl and halo;
$R^5$ is selected from the group consisting of H, OH, CN, nitro, $C_{1-8}$ alkyl, $OC_{1-8}$ alkyl and halo;
$R^6$ is selected from the group of H, OH, CN, $OC_{1-8}$ alkyl methyl, ethyl, propyl and butyl;
$R^7$ is selected from the group consisting of H, aryl, $C_{1-8}$ alkyl, OH, and $OC_{1-8}$ alkyl;
$R^8$ is selected from the group consisting of aryl, $C_{1-8}$ alkyl, OH, and $OC_{1-8}$ alkyl, wherein said $R^8$ is optionally substituted with 1 to 2 substituents selected from halo, nitro, OH, CN, $C_{1-4}$ alkyl, $OC_{1-4}$ alkyl, $NH_2$, and $NHC(O)OC(CH_3)_3$;
X is selected from the group consisting of O or NH, wherein when X is O, $R^6$ is other than OH; and,
the broken line represents an optional double bond.
According to some embodiments, $R^3$ is $CH_3$ or $R^3$ is CN or $R^3$ is $CH=CH_2$. In further embodiments, $R^2$ is H.
In yet further embodiments of the present invention, compounds of Formula (1) include:
a) 3-{4-[6-(3-Methoxy-phenyl)-8,9-dihydro-7H-benzocyclohepten-5-yl]-phenyl}-acrylic acid;
b) 3-{4-[6-(4-Methoxy-phenyl)-8,9-dihydro-7H-benzocyclohepten-5-yl]-phenyl}-acrylic acid;
c) 3-{4-[6-(3-Hydroxy-phenyl)-8,9-dihydro-7H-benzocyclohepten-5-yl]-phenyl}-acrylic acid;
d) 3-{4-[6-(4-Hydroxy-phenyl)-8,9-dihydro-7H-benzocyclohepten-5-yl]-phenyl}-acrylic acid;
e) 5-{2-[4-(1,2-Diphenyl-but-1-enyl)-phenyl]-vinyl}-1H-tetrazole;
f) 3-[4-(6-Phenyl-6,7,8,9-tetrahydro-5H-benzocyclohepten-5-yl)-phenyl]-acrylic acid;
g) 3-[4-(2-Hydroxy-6-phenyl-8,9-dihydro-7H-benzocyclohepten-5-yl)-phenyl]-acrylic acid;
h) 3-{4-[2-Hydroxy-6-(3-hydroxy-phenyl)-8,9-dihydro-7H-benzocyclohepten-5-yl]-phenyl}-acrylic acid;
i) 3-{4-[2-Hydroxy-6-(4-hydroxy-phenyl)-8,9-dihydro-7H-benzocyclohepten-5-yl]-phenyl}-acrylic acid;
j) 5-{2-[4-(6-Phenyl-8,9-dihydro-7H-benzocyclohepten-5-yl)-phenyl]-vinyl}-1H-tetrazole;
k) 5-{2-[4-(1,2-Diphenyl-but-1-enyl)-phenyl]-vinyl}-1-methyl-1H-tetrazole;
l) 5-(2-{4-[6-(3-Methoxy-phenyl)-8,9-dihydro-7H-benzocyclohepten-5-yl]-phenyl}-vinyl)-1H-tetrazole;
m) 3-[4-(6-Hydroxy-2-phenyl-3,4-dihydro-naphthalen-1-yl)-phenyl]-acrylic acid;

n) 3-[4-(6-Hydroxy-2-phenyl-1,2,3,4-tetrahydro-naphthalen-1-yl)-phenyl]-acrylic acid;
o) 3-[4-(6-Phenyl-8,9-dihydro-7H-benzocyclohepten-5-yl)-phenyl]-propionic acid;
p) 3-[4-(6-Hydroxy-2-phenyl-1,2,3,4-tetrahydro-naphthalen-1-yl)-phenyl]-acrylic acid;
q) 3-[4-(6-Hydroxy-2-phenyl-1,2,3,4-tetrahydro-naphthalen-1-yl)-phenyl]-acrylic acid;
r) 3-[4-(3-Phenyl-2H-chromen-4-yl)-phenyl]-acrylic acid;
s) 3-[4-(2-Phenyl-3,4-dihydro-naphthalen-1-yl)-phenyl]-acrylic acid;
t) 3-[4-(2-Phenyl-1,2,3,4-tetrahydro-naphthalen-1-yl)-phenyl]-acrylic acid;
u) 3-[4-(6-Phenyl-8,9-dihydro-7H-benzocyclohepten-5-yl)-phenyl]-acrylic acid;
v) N-{3-[4-(1,2-Diphenyl-but-1-enyl)-phenyl]-acryloyl}-methanesulfonamide;
w) N-{3-[4-(1,2-Diphenyl-but-1-enyl)-phenyl]-acryloyl}-benzenesulfonamide;
x) N-{3-[4-(1,2-Diphenyl-but-1-enyl)-phenyl]-acryloyl}-C-phenyl-methanesulfonamide;
y) N-{3-[4-(1,2-Diphenyl-but-1-enyl)-phenyl]-acryloyl}-3-nitro-benzenesulfonamide;
z) N-{3-[4-(1,2-Diphenyl-but-1-enyl)-phenyl]-acryloyl}-4-nitro-benzenesulfonamide;
aa) N-{3-[4-(1,2-Diphenyl-but-1-enyl)-phenyl]-acryloyl}-2-methyl-benzenesulfonamide;
ab) N-{3-[4-(1,2-Diphenyl-but-1-enyl)-phenyl]-acryloyl}-4-methyl-benzenesulfonamide;
ac) N-{3-[4-(1,2-Diphenyl-but-1-enyl)-phenyl]-acryloyl}-2-nitro-benzenesulfonamide;
ad) N-{3-[4-(1,2-Diphenyl-but-1-enyl)-phenyl]-acryloyl}-C,C,C-trifluoro-methanesulfonamide;
ae) N-{3-[4-(1,2-Diphenyl-but-1-enyl)-phenyl]-acryloyl}-4-methoxy-benzenesulfonamide;
af) 4-Chloro-N-{3-[4-(1,2-diphenyl-but-1-enyl)-phenyl]-acryloyl}-benzenesulfonamide;
ag) 4-Cyano-N-{3-[4-(1,2-diphenyl-but-1-enyl)-phenyl]-acryloyl}-benzenesulfonamide;
ah) N-{3-[4-(1,2-Diphenyl-but-1-enyl)-phenyl]-acryloyl}-3-trifluoromethyl-benzenesulfonamide;
ai) 2-Chloro-N-{3-[4-(1,2-diphenyl-but-1-enyl)-phenyl]-acryloyl}-benzenesulfonamide;
aj) 3-Chloro-N-{3-[4-(1,2-diphenyl-but-1-enyl)-phenyl]-acryloyl}-benzenesulfonamide;
ak) N-{3-[4-(2-Phenyl-3,4-dihydro-naphthalen-1-yl)-phenyl]-acryloyl}-methanesulfonamide;
al) N-{3-[4-(2-Phenyl-3,4-dihydro-naphthalen-1-yl)-phenyl]-acryloyl}-benzenesulfonamide;
am) N-{3-[4-(3-Phenyl-2H-chromen-4-yl)-phenyl]-acryloyl}-methanesulfonamide;
an) N-{3-[4-(3-Phenyl-2H-chromen-4-yl)-phenyl]-acryloyl}-benzenesulfonamide;
ao) 4-{3-[4-(1,2-Diphenyl-but-1-enyl)-phenyl]-acryloylsulfamoyl}-benzoic acid methyl ester;
ap) N-{3-[4-(1,2-Diphenyl-but-1-enyl)-phenyl]-acryloyl}-2-trifluoromethyl-benzenesulfonamide;
aq) N-{3-[4-(1,2-Diphenyl-but-1-enyl)-phenyl]-acryloyl}-3-methyl-benzenesulfonamide;
ar) N-{3-[4-(1,2-Diphenyl-but-1-enyl)-phenyl]-acryloyl}-4-hydroxy-benzenesulfonamide;
as) N-{3-[4-(1,2-Diphenyl-but-1-enyl)-phenyl]-acryloyl}-3-methoxy-benzenesulfonamide;
at) N-{3-[4-(1,2-Diphenyl-but-1-enyl)-phenyl]-acryloyl}-4-trifluoromethyl-benzenesulfonamide;
au) N-{3-[4-(1,2-Diphenyl-but-1-enyl)-phenyl]-acryloyl}-3-hydroxy-benzenesulfonamide;
av) N-(2-Cyano-ethyl)-3-[4-(1,2-diphenyl-but-1-enyl)-phenyl]-acrylamide;
aw) N-{3-[4-(6-Phenyl-8,9-dihydro-7H-benzocyclohepten-5-yl)-phenyl]-acryloyl}-methanesulfonamide;
ax) N-{3-[4-(6-Phenyl-8,9-dihydro-7H-benzocyclohepten-5-yl)-phenyl]-acryloyl}-benzenesulfonamide;
ay) C-Phenyl-N-{3-[4-(2-phenyl-3,4-dihydro-naphthalen-1-yl)-phenyl]-acryloyl}-methanesulfonamide;
az) C-Phenyl-N-{3-[4-(6-phenyl-8,9-dihydro-7H-benzocyclohepten-5-yl)-phenyl]-acryloyl}-methanesulfonamide;
ba) 3-Chloro-propane-1-sulfonic acid {3-[4-(1,2-diphenyl-but-1-enyl)-phenyl]-acryloyl}-amide;
bb) (4-{3-[4-(1,2-Diphenyl-but-1-enyl)-phenyl]-acryloylsulfamoyl}-phenyl)-carbamic acid tert-butyl ester;
bc) 3-Piperidin-1-yl-propane-1-sulfonic acid {3-[4-(1,2-diphenyl-but-1-enyl)-phenyl]-acryloyl}-amide;
bd) 4-Amino-N-{3-[4-(1,2-diphenyl-but-1-enyl)-phenyl]-acryloyl}-benzenesulfonamide;
be) Ethanesulfonic acid {3-[4-(1,2-diphenyl-but-1-enyl)-phenyl]-acryloyl}-amide;
bf) 2-Dimethylamino-N-(4-{3-[4-(1,2-diphenyl-but-1-enyl)-phenyl]-acryloylsulfamoyl}-phenyl)-acetamide;
bg) Propane-2-sulfonic acid {3-[4-(1,2-diphenyl-but-1-enyl)-phenyl]-acryloyl}-amide;
bh) N-{3-[4-(1,2-Diphenyl-but-1-enyl)-phenyl]-acryloyl}-C-(4-fluoro-phenyl)-methanesulfonamide;
bi) 4-{3-[4-(1,2-Diphenyl-but-1-enyl)-phenyl]-acryloylsulfamoyl}-benzoic acid;
bj) N-(4-{3-[4-(1,2-Diphenyl-but-1-enyl)-phenyl]-acryloylsulfamoyl}-phenyl)-acetamide;
bk) 2,2,2-Trifluoro-ethanesulfonic acid {3-[4-(1,2-diphenyl-but-1-enyl)-phenyl]-acryloyl}-amide;
bl) 3-Chloro-propane-1-sulfonic acid {3-[4-(6-phenyl-8,9-dihydro-7H-benzocyclohepten-5-yl)-phenyl]-acryloyl}-amide;
bm) C,C,C-Trifluoro-N-{3-[4-(6-phenyl-8,9-dihydro-7H-benzocyclohepten-5-yl)-phenyl]-acryloyl}-methanesulfonamide;
bn) 3-[4-(1,2-Diphenyl-but-1-enyl)-phenyl]-N-hydroxy-acrylamide;
bo) 3-[4-(1,2-Diphenyl-but-1-enyl)-phenyl]-N-methoxy-acrylamide;
bp) 3-Piperidin-1-yl-propane-1-sulfonic acid {3-[4-(6-phenyl-8,9-dihydro-7H-benzocyclohepten-5-yl)-phenyl]-acryloyl}-amide;
bq) C-(4-Fluoro-phenyl)-N-{3-[4-(6-phenyl-8,9-dihydro-7H-benzocyclohepten-5-yl)-phenyl]-acryloyl}-methanesulfonamide;
br) Thiophene-2-sulfonic acid {3-[4-(1,2-diphenyl-but-1-enyl)-phenyl]-acryloyl}-amide;
bs) N-{3-[4-(1,2-Diphenyl-but-1-enyl)-phenyl]-acryloyl}-C-(4-trifluoromethyl-phenyl)-methanesulfonamide; and, bt) 4-{3-[4-(1,2-Diphenyl-but-1-enyl)-phenyl]-acryloylsulfamoyl}-N-methyl-benzamide.

This invention also provides pharmaceutical compositions for the treatment and/or prevention of breast, uterine, ovarian, prostrate and colon cancer, osteoporosis, cardiovascular disease, and benign proliferative disorders. Pharmaceutical compositions of the present invention include any of the above compounds and a pharmaceutically acceptable carrier.

Another embodiment of the present invention provides a method of treating breast, uterine, ovarian, prostate and colon cancer, osteoporosis, cardiovascular disease, endometriosis, uterine fibroid, Alzheimer's disease, macular degeneration, urinary incontinence, type II diabetes, and benign proliferative disorders, comprising: administering to a host in need of such treatment a therapeutically effective amount of a compound of Formula (I).

The present invention further provides methods of modulating the estrogen receptor in a patient comprising the step of administering to the patient a therapeutically effective amount of a compound of Formula (I).

Also included in the present invention are compounds of Formula (II):

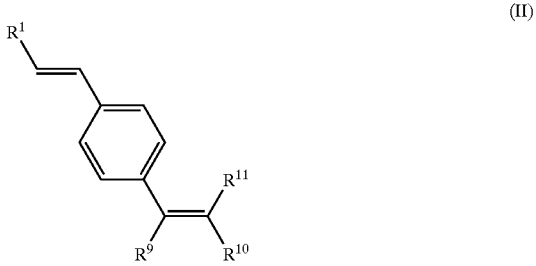

(II)

wherein $R^1$ is selected from the group consisting of

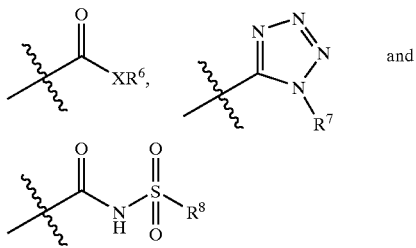

and $R^6$ is selected from the group of H, methyl, ethyl, propyl and butyl;

$R^7$ is selected from the group consisting of aryl and $C_{1-8}$ alkyl, optionally substituted with one or more substituent groups;

$R^8$, $R^9$, $R^{10}$ and $R^{11}$ are the same or different, and are independently selected from the group consisting of: H, $C_{1-8}$ alkyl, $C_{2-8}$ alkenyl, $C_{2-8}$ alkynyl, aryl, $NO_2$, $NH_2$, OH, $OC_{1-8}$ alkyl, CHO, COOH, halo and CN, wherein said $R^8$ is optionally substituted with 1 to 2 substituents selected from halo, nitro, OH, CN, $C_{1-4}$ alkyl, $OC_{1-4}$ alkyl, $NH_2$, and $NHC(O)OC(CH_3)_3$.

Definitions

The compounds of the present invention may contain an asymmetrically substituted carbon atom, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated.

The term "alkyl" is intended to include both branched and straight-chain saturated aliphatic hydrocarbon groups having the specified number of carbon atoms. Example s of alkyl include, but are not limited to, methyl, ethyl, n-propyl, i-propyl, n-butyl, s-butyl, t-butyl, n-pentyl, and s-pentyl. In addition, the term is intended to include both unsubstituted and substituted alkyl groups, the latter referring to alkyl moieties having one or more hydrogen substituents replaced by, but not limited to halogen, hydroxyl, carbonyl, alkoxy, ester, ether, cyano, phosphoryl, amino, imino, amido, sulfhydryl, alkythio, thioester, sulfonyl, nitro, heterocyclo, aryl or heteroaryl. It will also be understood by those skilled in the art that the substituted moieties themselves can be substituted as well when appropriate. The term "haloalkyl" as used herein refers to an alkyl substituted with one or more halogens.

The terms "linear and cyclic heteroalkyl" are defined in accordance with the term "alkyl" with the suitable replacement of carbon atoms with some other atom such as nitrogen or sulfur which would render a chemically stable species.

The terms "halo" or "halogen" as used herein refer to fluoro, chloro, bromo and iodo. The term "aryl" is intended to mean an aromatic cyclic or bicyclic ring structure containing from 5 to 13 ring atoms, including compounds, such as, for example phenyl, indanyl and naphthyl. In addition, the term aryl is intended to include both unsubstituted and substituted aryl groups, the latter referring to aryl moieties having one or more hydrogen substituents replaced by, for example, halogen, hydroxyl, carbonyl, alkoxy, keto, ester, ether, cyano, phosphoryl, amino, imino, amido, sulfhydryl, alkythio, thioester, sulfonyl, nitro, and/or heterocyclo. The term "haloaryl" as used herein refers to an aryl mono, di or tri substituted with halogen atoms.

As used herein, the terms "cycloalkyl" "bicycloalkyl" "carbocycle" or "carbocyclic residue" are intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" or "heterocyclyl" is intended to mean a stable 5- to 7-membered monocyclic or bicyclic or 7- to 10-membered bicyclic heterocyclic ring which is partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, xanthenyl. Preferred heterocycles include, but are not limited to, pyridinyl, piperidinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The term "heteroaryl" further includes a 5-membered or 6-membered heterocyclic aromatic group that can optionally carry a fused benzene ring and that can be unsubstituted or substituted.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, meglumine, lysine, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, the disclosure of which is hereby incorporated by reference in it's entirety as though set forth in full.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs", as the term is used herein, are intended to include any covalently bonded carriers which release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfydryl group, respectively. Examples of prodrugs include, but are not limited to, acetate, formate, and benzoate derivatives of alcohol and amine functional groups in the compounds of the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

For purposes of the present invention the term "substitutent group" refers to $R^1$, $R^2$, $R^3$, $R^4$, $R^5$, $R^6$, and $R^7$ or any group selected from the group consisting of —$NO_2$, —$NH_2$, —COOH, —CHO, OH, alhoxy keto, —$SO_2$, halogen, hydrogen, —CN and aryl.

As used herein, the term "anti cancer" or "antiproliferative" agent includes, but is not limited to, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, hydroxyurea and the compounds disclosed in U.S. Pat. No. 5,681,835, issued to Timothy Wilson on Mar. 2, 1999. THF is an abbreviation for tetrahydrofuran; DME is an abbreviation for ethylene glycol dimethyl ether.

For purposes of the present invention the term "host" refers to mammals including humans.

Dosage and Formulation

The selective estrogen receptor modulator compounds of this invention can be administered as treatment for or prevention of cancer or other disease states by any means that produces contact of the active agent with the agent's site of action in the body of a mammal. They can be administered by any conventional means available for use in conjunction with pharmaceuticals, either as individual therapeutic agents or in combination with other compounds according to the present invention and/or other therapeutic agents, such as anti-cancer or anti-proliferative agents. When used in combination, the therapeutic agents may be administered together or separately so long as the therapeutic agents, or their active metabolites, are present in the host during an overlapping time period. The therapeutic agents can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Anti-oxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, 18th ed., Mack Publishing Company, Easton, Pa., 1990, a standard reference text in this field, the disclosure of which is hereby incorporated by reference.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used. Isolation of the desired compounds of this invention can be achieved using standard chromatographic techniques known to those skilled in the art.

Depending on the structure of the final product, it will be appreciated by those skilled in the art that protecting groups or precursor functionality convertable to the desired groups may be desireable. Protecting groups and their use in synthesis are described in Green and Wuts, Protective Groups in Organic Synthesis, (Wiley 1991).

Scheme 1: General Synthesis of Acylsulfonamide II

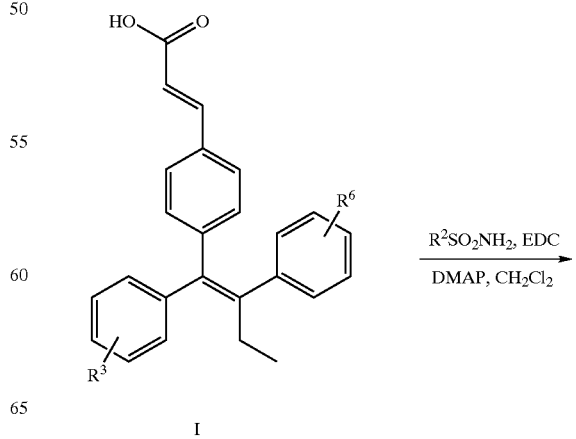

I

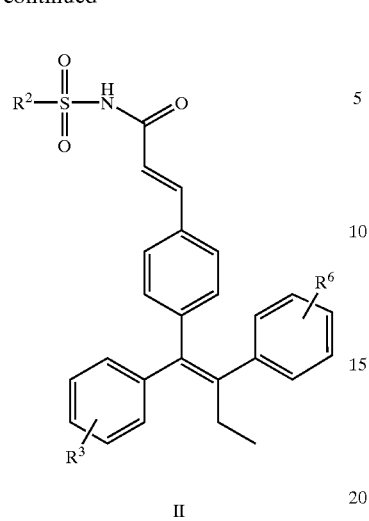

II

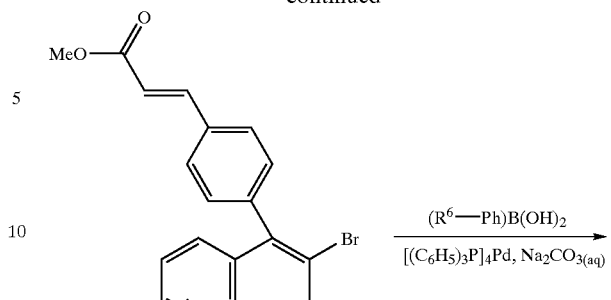

V

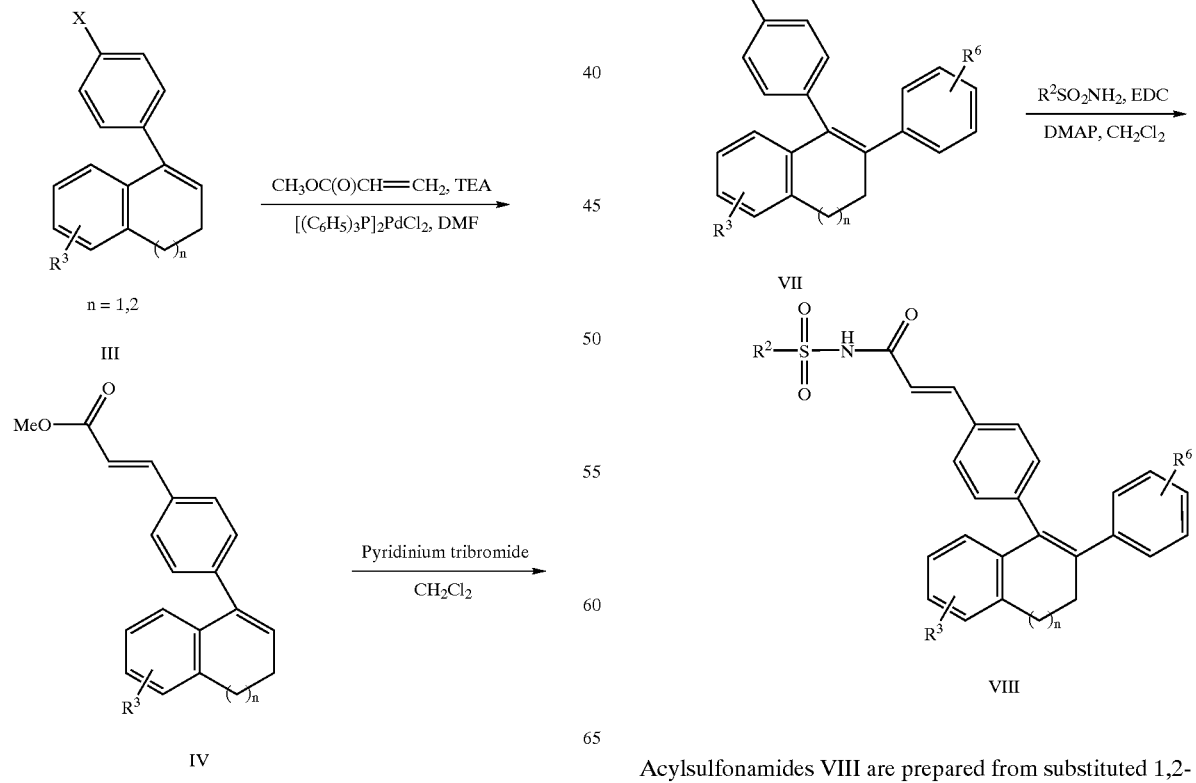

Conversion of substituted acrylic acid I to an acylsulfonamide II employs a coupling reaction with a sulfonamide $R^2SO_2NH_2$ (Scheme 1). The coupling reaction is performed in the presence of DMAP and 1-(3-dimethyl-aminopropyl)-3-ethylcarbodiimide hydrochloride (EDC). Other reagents, besides EDC, which can be employed in this coupling reaction include HATU, TBTU, BOP, pyBOP, EDC, CDI, and DCC. Suitable solvents for the coupling reaction include $CH_2Cl_2$.

Scheme 2: General Synthesis of Acylsulfonamide VIII

Acylsulfonamides VIII are prepared from substituted 1,2-dihydronaphthalene III or substituted dihydro benzocycloheptene III in five steps: 1) Heck coupling, 2) halogenation, 3) Suzuki coupling, 4) hydrolysis, and 5) sulfonylation reaction.

1. Heck Coupling Reaction. Substituted 1,2-dihydronaphthalene III or substituted dihydro benzocycloheptene III (X=halo, tosylate, mesylate or triflate) is coupled with a methyl acrylate ester in the presence of a palladium catalyst and a base to form benzocyclohexene or dihydro benzocycloheptene IV.

Solvents for the Heck reaction are well known to the skilled artisan and include amides (e.g., dimethylformamide, dimethylacetamide, N-methylpyrrolidone), nitriles (e.g., acetonitrile, propionitrile, butyronitrile), ethers (e.g., dimethoxyethane, tetrahydrofuran), and hydrocarbons (e.g., cyclohexane, benzene, toluene, xylene)

Palladium catalysts suitable for the Heck coupling reaction include, but are not limited to, $Pd(OAc)_2$, $PdCl_2(CH_3CN)_2$, or $Pd_2(dba)_3$.

Bases which are useful in the Heck reaction include alkaline metal carbonates and hydrogen carbonates, alkaline metal acetates, alkaline metal phosphates, and tertiary amines. Examples of bases for the Heck coupling reaction include TEA, PMP (1,2,2,6,6-pentamethylpiperidine), $Na_2CO_3$, $Ag_2CO_3$, or $NaHCO_3$. Preferred bases are tertiary amines.

After the reaction is complete, the catalyst may be obtained as a solid and separated off by filtration. The crude product is freed of the solvent or the solvents and is subsequently purified by methods known to those skilled in the art e.g. by chromatography.

For an example of the preparation of dihydro benzocycloheptene IV, see J. Chem. Soc. B, 1969, 638–643.

2. Halogenation

Halogenation of benzocyclohexene or dihydro benzocycloheptene IV can be performed by employing a variety of electrophilic halogenating reagents such as pyridinium bromide perbromide or NBS to afford halo benzocyclohexene and halo dihydro benzocycloheptene V. Halogenation reactions are well known to those skilled in the art and are described in the chemical literature. See for example: Larock, R. C. Comprehensive Organic Transformations, VCH Publishers, New York, 1989.

3. Suzuki Coupling Reaction

A Suzuki coupling of a halo benzocyclohexene or a halo dihydro benzocycloheptene V with a boronic acid $(R^6\text{-Ph})B(OH)_2$ in the presence of a palladium catalyst and a base provides bis-aryl substituted benzocyclohexene or bis-aryl substituted dihydro benzocycloheptene VI. Suitable solvents for this coupling include, but are not limited to, THF, $H_2O$, DMSO, $Et_2O$, toluene, DMF, dioxane and ethanol, i-PrOH, or a combination of two or more of these solvents. The reaction is carried out in the presence of a palladium catalyst, for example, $[(C_6H_5)_3P]_4Pd$, $[(C_6H_5)_3P]_2PdCl_2$, $PdCl_2(dppf)$, or $Pd(OAc)_2$. Suitable bases for the Suzuki coupling reaction include TEA, KOH, TlOH, $Na_2CO_3$, $Cs_2CO_3$, and $K_2CO_3$. See, for example, Miyaura, N., Suzuki, A. *Chem. Rev.* 1995, 95, 2457–2483; Suzuki, A., *J. Organometallic Chem.* 1999, 576, 147–168; and Suzuki, A. in *Metal-catalyzed Cross-coupling Reactions*, Diederich, F., and Stang, P. J., Eds.; Wiley-VCH: New York, 1998, pp. 49–97.

4. Hydrolysis.

Conversion of bis-aryl substituted benzocyclohexene or bis-aryl substituted dihydro benzocycloheptene VI to the corresponding substituted acrylic acid VII is carried out using standard hydrolysis reaction. Suitable bases include hydroxides or carbonates in an ether, alcohol, or aqueous alcohol or aqueous ether solvent systems. See Larock, R. C., Comprehensive Organic Transformations, VCH Publishers, New York, 1989.

5. Sulfonylation.

Conversion of substituted acrylic acid VII to an acylsulfonamide VII employs a coupling reaction with a sulfonamide $R^2SO_2NH_2$. See the experimental section of Scheme 1.

Scheme 3: General Synthesis of Benzopyran XIII

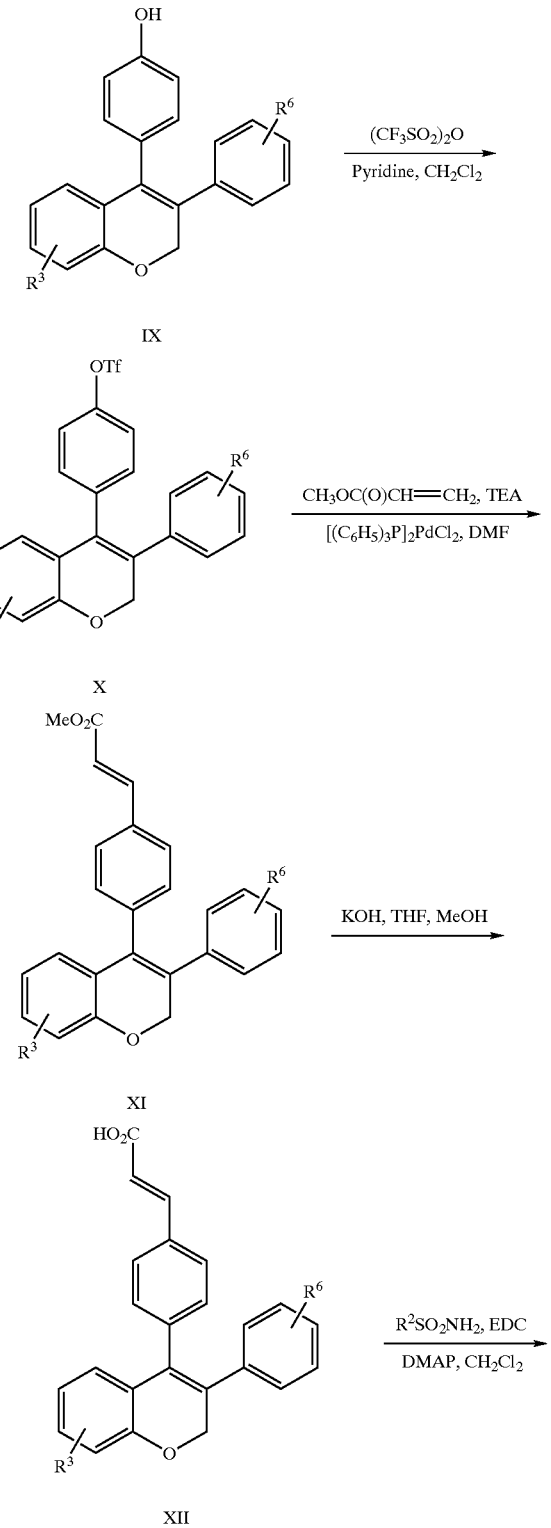

-continued

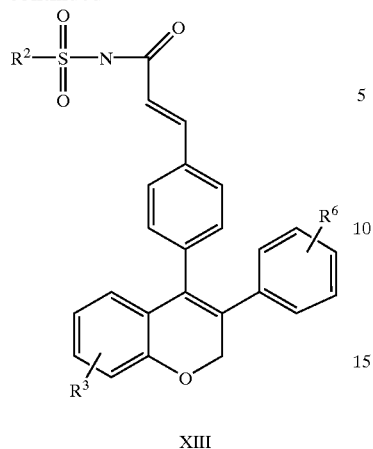

XIII

Benzopyran XIII can be prepared from substituted 2H-chromene IX using a reaction sequence similar to that of Scheme 2 with several modifications. One is that the halogenation and suzuki coupling steps are not needed in the synthesis of benzopyran XIII since the phenyl bearing substituent $R^6$ is already present in the starting material 2H-chromene IX. The second modification is that a reaction to convert the OH group 2H-chromene IX to an tosylate, mesylate or triflate is needed for a subsequent coupling reaction. The preparation of benzopyran XIII from substituted 2H-chromene IX takes four steps: 1) preparation of aryl-X coupling partner for a subsequent Heck reaction, e.g. trifluoro-methanesulfonyl ester, 2) Heck coupling reaction, 3) hydrolysis, and 4) sulfonylation. Preparation of trifluoromethanesulfonyl ester X from phenol IX (step 1) is well known in the literature. See: Larock, R. C. Comprehensive Organic Transformations, VCH Publishers, New York, 1989. Subsequent transformations of aryl-OTf X to Benzopyran XIII (steps 2–4) can be accomplished using the method described in Scheme 2.

Scheme 4: General methods for synthesis of tetrazole XV

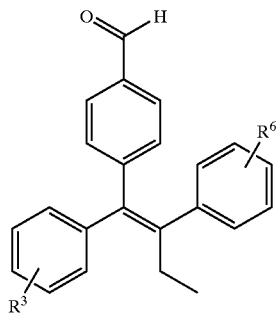

XIII

-continued

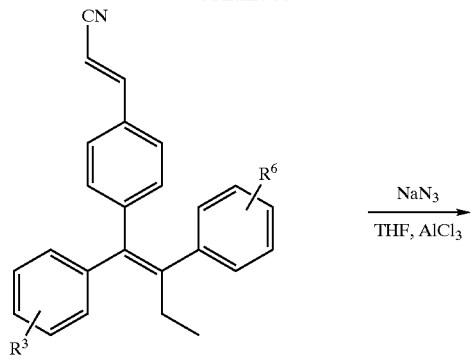

XIV

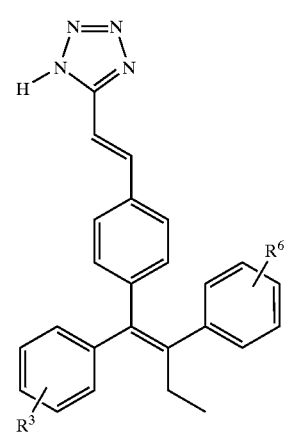

Tetrazole XV is prepared from benzaldehyde XIII in two steps. The first step is a 1,2-addition of acetonitrile to benzaldehyde XIII followed by elimination of water to provide cinnamonitrile XIV. A base such as KOH is used to deprotonate the hydrogen of the methyl group of acetonitrile in this reaction. The second step involves an addition of an azide to cinnamonitrile XIV to form tetrazole XV in the presence of a Lewis acid catalyst. Optionally, compound XV may be further functionalized by methylation of the tetrazole group. Such N-methylation is well known in the art.

Scheme 5: Synthesis of dihydro benzocycloheptenyl tetrazole XIX

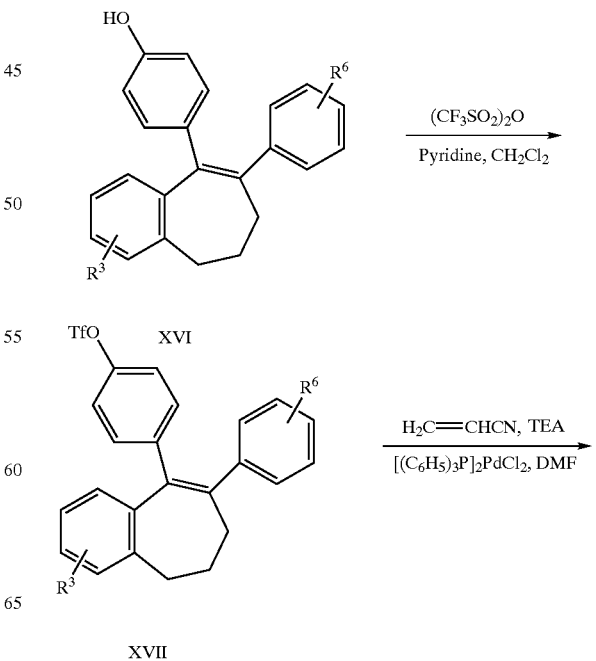

XVII

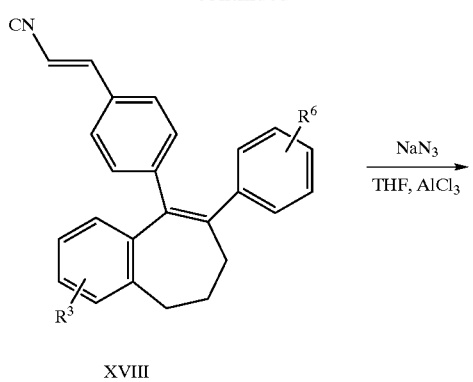

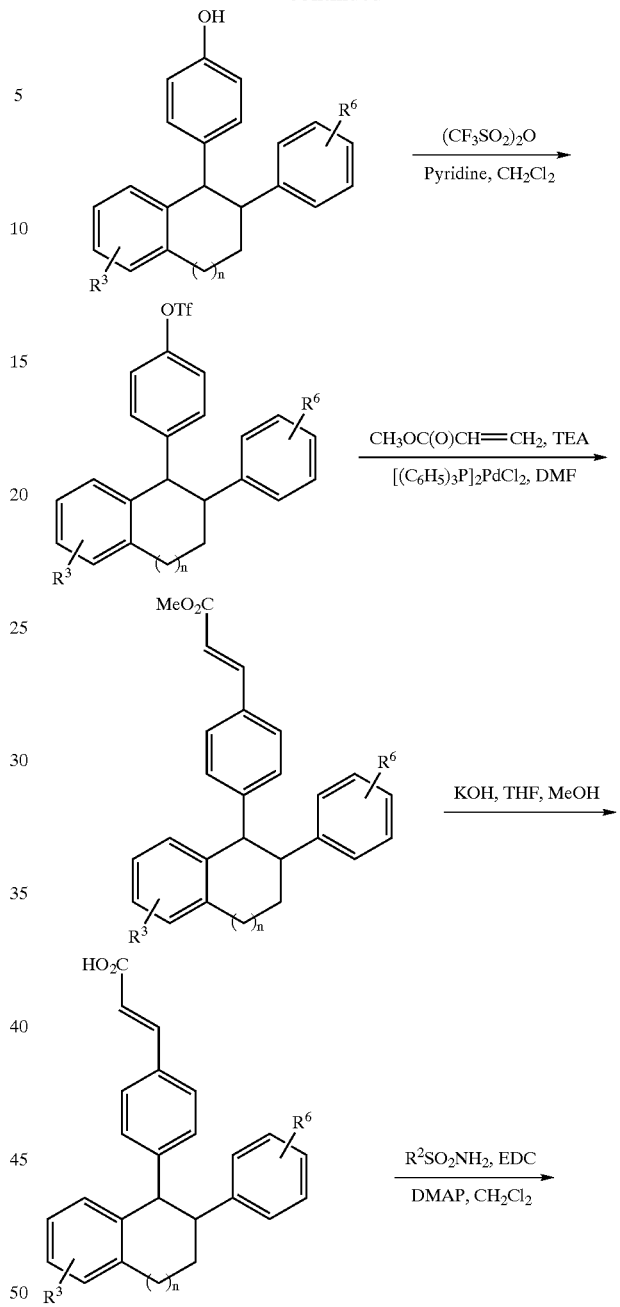

Dihydro benzocycloheptenyl tetrazole XIX can be prepared from dihydro benzocycloheptenyl phenol XVI in three steps. Step 1) preparation of triflate XVII; step 2) Heck coupling, and step 3) tetrazole formation. The preparation of tetrazole XIX involves the addition of an azide to cinnamonitrile XVIII in the presence of a Lewis acid catalyst. Optionally, compound XIX may be further functionalized by methylation of the tetrazole group. See Scheme 4.

Scheme 6: General Synthesis of Tetrahydronaphthalenes and Tetrahydrobenzocycloheptenes

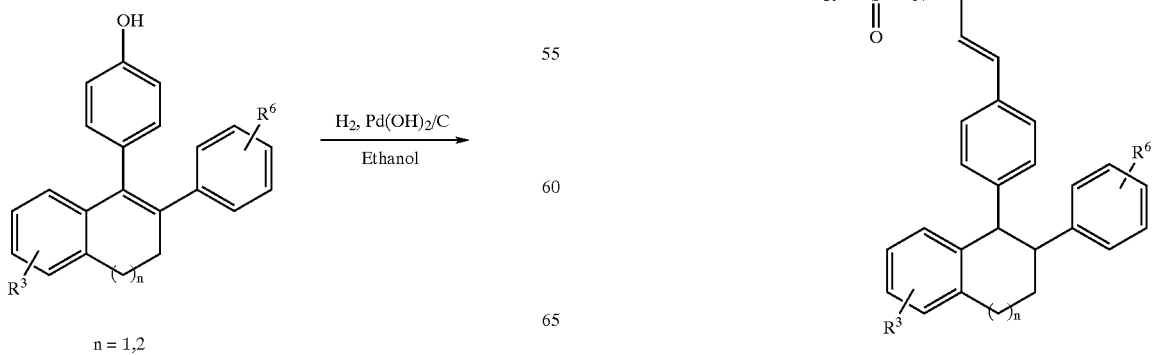

EXAMPLES

The invention can be further understood by the following examples. Other features of the invention will become apparent to those skilled in the art during the following description and exemplary embodiments that are given for illustration and are not intended to be limiting thereof.

Example I

Preparation of N-{3-[4-(1,2-diphenyl-but-1-enyl)-phenyl]-acryloyl}-methanesulfonamide 1b

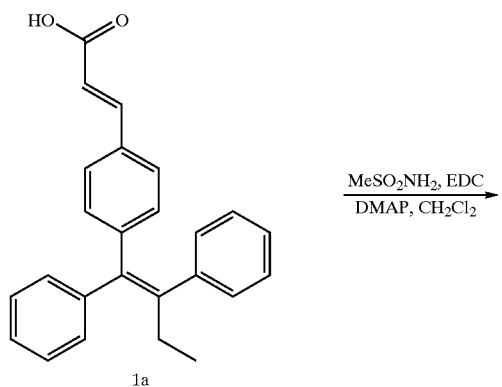

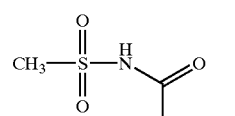

Procedure 1, Method A. To a solution of 3-[4-(Z)-(1,2-diphenylbut-1-enyl)phenyl]-acrylic acid (1a, compound I, $R^3$=H, $R^6$=H)(666 mg, 1.87 mmol) in $CH_2Cl_2$ (10 mL) was added methanesulfonamide (711 mg, 7.47 mmol), 1-[3-(dimethylamino)propyl]-3-ethylcarbodiimide hydrochloride (EDC)(540 mg, 2.82 mmol), and 4-dimethylaminopyridine (344 mg, 2.82 mmol). After stirring overnight the mixture was acidified with 1N HCl, and was extracted with EtOAc. The combined organic layers were washed with brine and dried ($MgSO_4$). The solvent was removed under reduced pressure and the residue was chromatographed (silica gel, 5% methanol/$CH_2Cl_2$) to give the acylsulfonamide (1b) as a white solid (695 mg, 86%): $^1$H NMR ($CDCl_3$) δ 7.61 (d, J=15.7 Hz, 1H), 7.39–7.09 (m, 12H), 6.91 (d, J=8.4 Hz, 2H), 6.23 (d, J=15.7 Hz, 1H), 3.34 (s, 3H), 2.48 (q, J=7.3 Hz, 2H), 0.94 (t, J=7.3 Hz, 3H); ESI m/z: 430 (M−H⁻, 100%).

Example II

Preparation of N-{3-[4-(1,2-diphenyl-but-1-enyl)-phenyl]-acryloyl}-benzenesulfonamide 1c

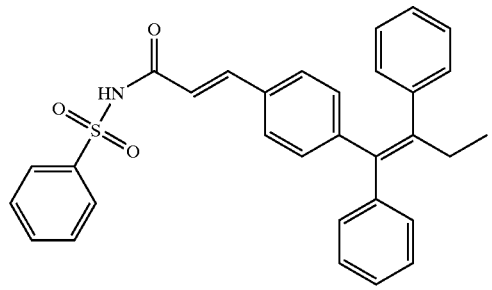

Prepared from the coupling of 1a (compound I, $R^3$=H, $R^6$=H) and benzene sulfonamide by the method described in Procedure 1, Method A. Yield (76%); $^1$H NMR ($CDCl_3$) δ 8.41 (br. s, 1H), 8.08 (d, J=8.4 Hz, 2H), 7.65–7.07 (m, 16H), 6.86 (d, J=8.4 Hz, 2H), 6.23 (d, J=15.7 Hz, 1H), 2.46 (q, J=7.3 Hz, 2H), 0.92 (t, J=7.3 Hz, 3H); ESI m/z: 492 (M−H⁻, 100%).

Example III

Preparation of N-{3-[4-(1,2-diphenyl-but-1-enyl)-phenyl]-acryloyl}-C-phenyl-methanesulfonamide 1d

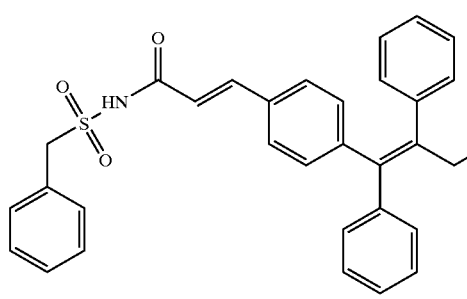

Prepared from the coupling of 1a (compound I, $R^3$=H, $R^6$=H) and •-toluene sulfonamide by the method described in Procedure 1, Method A. Yield (61%); $^1$H NMR ($CDCl_3$) δ 7.59 (d, J=15.7 Hz, 1H), 7.39–7.10 (m, 17H), 6.90 (d, J=8.4 Hz, 2H), 6.13 (d, J=15.7 Hz, 1H), 4.68 (s, 2H), 2.48 (q, J=7.3 Hz, 2H), 0.94 (t, J=7.3 Hz, 3H); ESI m/z: 506 (M−H⁻, 100%)

Example IV

Preparation of intermediate 3-[4-(8,9-Dihydro-7H-benzocyclohepten-5-yl)-phenyl]-acrylic acid methyl ester 2b

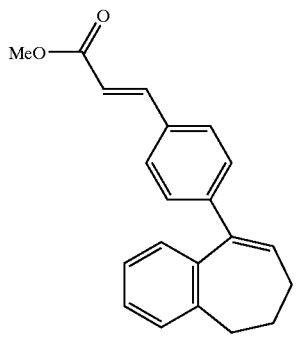

To a solution of 9-(4-bromophenyl)-6,7-dihydro-5H-benzocycloheptene (2a, compound III, $R^3$=H, X=Br, n=2) (12.38 g, 41 mmol) in DMF (30 mL) was added methyl acrylate (38.2 g, 444 mmol), triethylamine (29.0 g, 286 mmol), and bis(triphenylphosphine)palladium(II) chloride (7.0 g, 10.0 mmol). The mixture was placed in a pressure bottle and heated at 100° C. for 4 days. The solvent was removed under reduced pressure and the residue was chromatographed (silica gel, 7.5 to 15% EtOAc/hexanes) to give the ester (2b) as a white solid (11.4 g, 90%): $^1$H NMR (CDCl$_3$) δ 7.69 (d, J=15.7 Hz, 1H), 7.45 (d, J=8.1 Hz, 2H), 7.24 (m, 5H), 6.98 (m, 1H), 6.52 (t, J=7.3 Hz, 1H), 6.43 (d, J=15.7 Hz, 1H), 3.81 (s, 3H), 2.65 (t, J=7.0 Hz, 2H), 2.17 (m, 2H), 1.98 (m, 2H); APcI m/z: 346 (M+H+CH$_3$CN$^+$, 100%).

Example V

Preparation of intermediate 3-[4-(6-Bromo-8,9-dihydro-7H-benzocyclohepten-5-yl)-phenyl]-acrylic acid methyl ester 2c

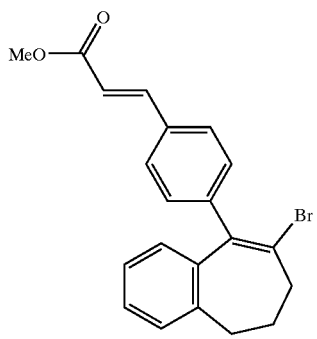

To a solution of the olefin (2b) (5.44 g, 17.9 mmol) in CH$_2$Cl$_2$ (300 mL) at 0° C. was added pyridinium bromide perbromide (90%, 7.0 g, 19.6 mmol) in portions over 0.5 h. After stirring 1 h the solution was washed with water, sat. NaHSO$_3$, water and was dried (MgSO$_4$). The solvent was removed under reduced pressure to give the bromide (2c) as an oil (6.85 g, 100%): $^1$H NMR (CDCl$_3$) δ 7.69 (d, J=16.1 Hz, 1H), 7.50 (d, J=8.1 Hz, 2H), 7.20 (m, 5H), 6.80 (d, J=7.3 Hz, 1H), 6.43 (d, J=16.1 Hz, 1H), 3.81 (s, 3H), 2.79 (t, J=7.0 Hz, 2H), 2.60 (t, J=7.0 Hz, 2H), 2.30 (m, 2H); APcI m/z: 424 (M+H+CH$_3$CN$^+$, 100%).

Example VI

Preparation of intermediate 3-[4-(6-Phenyl-8,9-dihydro-7H-benzocyclohepten-5-yl)-phenyl]-acrylic acid methyl ester 2d

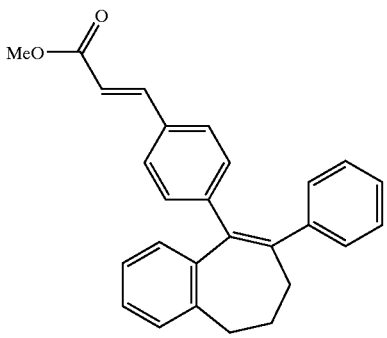

To a solution of the bromide (2c) (6.85 g, 17.9 mmol) in DME (125 mL) was added benzene boronic acid (3.25 g, 26.8 mmol), tetrakis(triphenylphosphine)palladium(0) (2.1 g, 1.8 mmol), and 2N aqueous sodium carbonate(13.5 mL). After refluxing overnight the solvent was removed under reduced pressure and the residue was chromatographed (silica gel, 7.5 EtOAc/hexanes to 100% EtOAc) followed by recrystalization from EtOAc to give (2d) as a white solid (4.24 g, 62%): $^1$H NMR (CDCl$_3$) δ 7.58 (d, J=16.1 Hz, 1H), 7.20 (m, 10H), 6.92 (d, J=8.1 Hz, 2H), 6.85 (dd, J=7.3, 1.1 Hz, 1H), 6.32 (d, J=16.1 Hz, 1H), 3.78 (s, 3H), 2.82 (t, J=7.0 Hz, 2H), 2.40 (t, J=7.0 Hz, 2H), 2.20 (m, 2H); APcI m/z: 422 (M+H+CH$_3$CN$^+$, 100%).

Example VII

Preparation of 3-[4-(6-Phenyl-8,9-dihydro-7H-benzo-cyclohepten-5-yl)-phenyl]-acrylic acid 2e

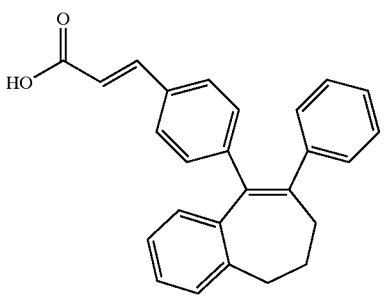

To a solution of ester (2d) (4.2 g, 11.0 mmol) in methanol (370 mL) and THF (225 mL) was added 1N KOH (188 mL). After stirring overnight the mixture was heated to 50° C. for 0.5 h and was allowed to cool to rt. After stirring 2 h the solvent was partially removed under reduced pressure, the mixture was acidified with 1N HCl, and was extracted with EtOAc. The combined organic layers were washed with water, brine and were dried (MgSO$_4$). The solvent was removed under reduced pressure and the residue was triturated (EtOAc) to give the acid (2e) as a white solid (3.86 g, 96%): $^1$H NMR (CD$_3$OD) δ 7.54 (d, J=15.7 Hz, 1H), 6.28 (d, J=8.1 Hz, 2H), 7.27–7.08 (m, 8H), 6.89 (d, J=8.1 Hz, 2H), 6.76 (dd, J=7.3, 1.1 Hz, 1H), 6.34 (d, J=15.7 Hz, 1H), 2.83 (t, J=7.0 Hz, 2H), 2.37 (t, J=7.0 Hz, 2H), 2.14 (m, 2H); ESI m/z: 365 (M−H$^−$, 100%).

Example VIII

Preparation of N-{3-[4-(6-phenyl-8,9-dihydro-7H-benzo-cyclohepten-5-yl)-phenyl]-acryloyl}-methanesulfonamide 2f

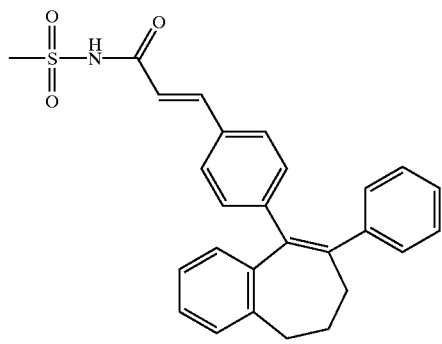

2f

Prepared from the coupling of 2e and methylsulfonamide by the method described in Procedure 1, Method A. Yield (68%); $^1$H NMR (CDCl$_3$) δ 7.66 (d, J=15.7 Hz, 1H), 7.18 (m, 10H), 6.95 (d, J=8.1 Hz, 2H), 6.84 (d, J=7.3 Hz, 1H), 6.28 (d, J=15.7 Hz, 1H), 3.36 (s, 3H), 2.82 (t, J=7.0 Hz, 2H), 2.41 (t, J=7.0 Hz, 2H), 2.19 (m, 2H); ESI m/z: 442 (M−H$^−$, 100%).

Example IX

Preparation of N-{3-[4-(6-phenyl-8,9-dihydro-7H-benzo-cyclohepten-5-yl)-phenyl]-acryloyl}-benzenesulfonamide 2 g

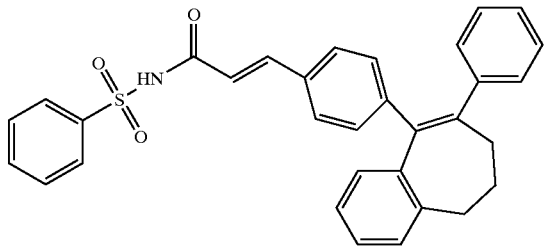

2g

Prepared from the coupling of 2e and benzene sulfonamide by the method described in Procedure 1, Method A. Yield (70%); $^1$H NMR (d$_6$-DMSO) δ 12.25 (s, 1H), 7.94 (d, J=7.3 Hz, 2H), 7.66 (m, 3H), 7.42 (d, J=15.7 Hz, 1H), 7.34–7.14 (m, 10H), 6.88 (d, J=8.1 Hz, 2H), 6.72 (d, J=7.3 Hz, 1H), 6.48 (d, J=15.7 Hz, 1H), 2.79 (m, 2H), 2.28 (m, 2H), 2.09 (m, 2H); ESI m/z: 504 (M−H$^−$, 100%).

Example X

C-Phenyl-N-{3-[4-(6-phenyl-8,9-dihydro-7H-benzo-cyclohepten-5-yl)-phenyl]-acryloyl}-methanesulfonamide 2h

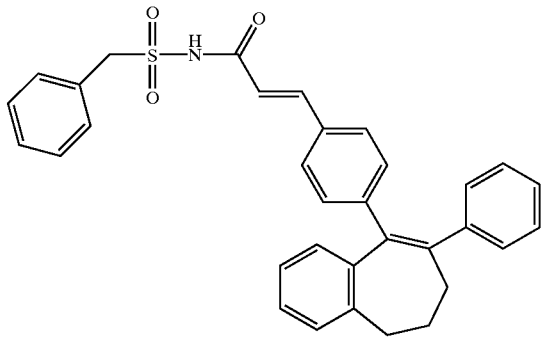

2h

Prepared from the coupling of 2e and •-toluene sulfonamide by the method described in Procedure 1, Method A. Yield (58%); ESI m/z: 518 (M−H$^−$, 100%).

Example XI

Preparation of intermediate 3-[4-(3,4-dihydro-naphthalen-1-yl)-phenyl]-acrylic acid methyl ester 2j

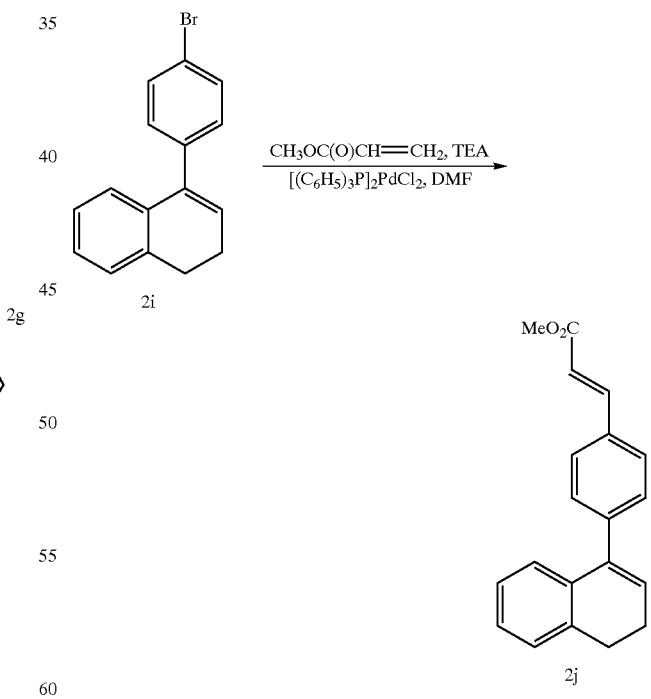

Prepared from the Heck coupling of 4-(4-bromophenyl)-1,2-dihydro-naphthalene (2i, compound III, R$^3$=H, X=Br, n=1) and methyl acrylate by the general method described for example 2b (J. Chem. Soc. B, 1969, 638–643). Yield 74%; APcI m/z: 332 (M+H+CH$_3$CN$^+$, 100%).

Example XII

Preparation of intermediate 3-[4-(2-bromo-3,4-dihydro-naphthalen-1-yl)-phenyl]-acrylic acid methyl ester 2k

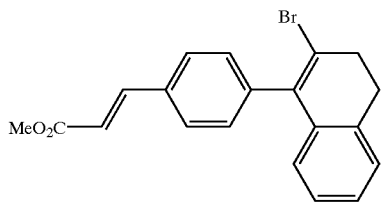

2k

Prepared by the bromination of 2j by the general method described for example 2c. Yield 100%; ApcI m/z: 410 (M+H+CH₃CN⁺, 100%).

Example XIV

Preparation of intermediate 3-[4-(2-phenyl-3,4-dihydro-naphthalen-1-yl)-phenyl]-acrylic acid methyl ester 2l

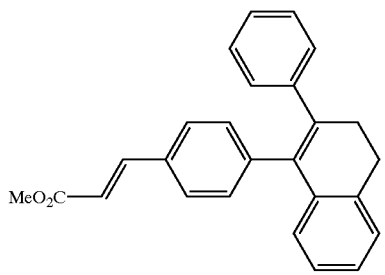

2l

Prepared from the coupling of 2k and benzene boronic acid, (R⁶—Ph)B(OH)₂ where R⁶=H, by the general method described for example 2d. Yield 50%; APcI m/z: 408 (M+H+ CH₃CN⁺, 100%).

Example XV

Preparation of intermediate 3-[4-(2-phenyl-3,4-dihydro-naphthalen-1-yl)-phenyl]-acrylic acid 2m

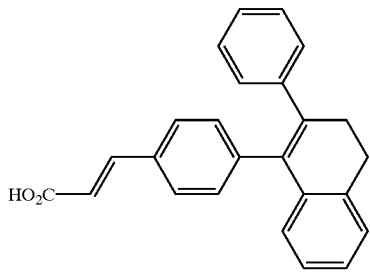

2m

Prepared from the saponification of ester 2l by the general method described for example 2e. Yield (77%). ¹H NMR (DMSO-d₆) δ 12.34 (s, 1H), 7.52 (m, 3H), 7.23–7.00 (m, 10H), 6.53 (d, J=6.5 Hz, 1H), 6.45 (d, J=15.7 Hz, 1H), 2.91 (br t, J=7.9 Hz, 2H), 2.71 (br t, J=7.9 Hz, 2H); ESI m/z: 351 (M−H⁻, 100%).

Example XVI

Preparation of N-{3-[4-(2-phenyl-3,4-dihydro-naphthalen-1-yl)-phenyl]-acryloyl}-methanesulfonamide 2n

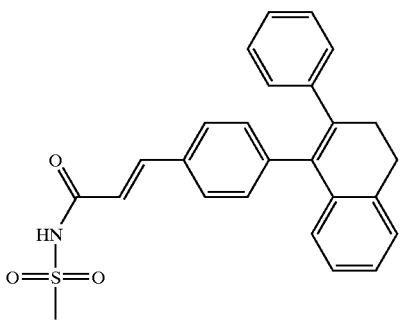

2n

Prepared from the coupling of 2m and methylsulfonamide by the method described in Procedure 1, Method A. Yield (57%); ESI m/z: 428 (M−H⁻, 100%).

Example XVII

Preparation of N-{3-[4-(2-phenyl-3,4-dihydro-naphthalen-1-yl)-phenyl]-acryloyl}-benzenesulfonamide 2o

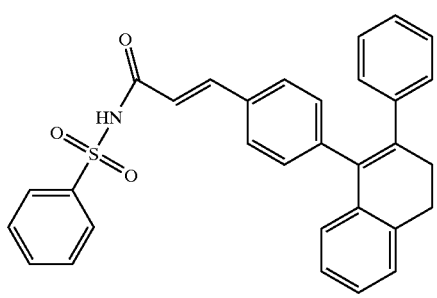

2o

Prepared from the coupling of 2m and benzene sulfonamide by the method described in Procedure 1, Method A. Yield (65%); ESI m/z: 490 (M−H⁻, 100%).

Example XVIII

Preparation of intermediate trifluoro-methanesulfonic acid 4-(3-phenyl-2H-chromen-4-yl)-phenyl ester 3b

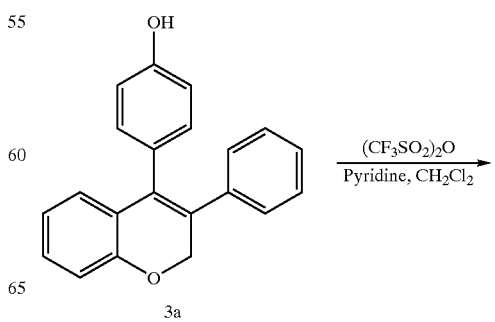

3a

-continued

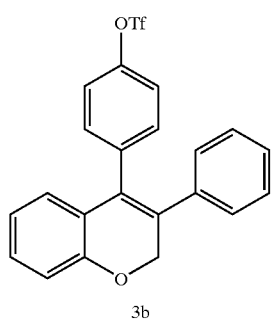

3b

To a solution of 4-(3-phenyl-2H-chromen-4-yl)-phenol (Justus Liebigs Ann. Chem. 1971, 744, 164–177.)(3a, compound IX, $R^3$=H, $R^6$=H) (3.18 g, 10.58 mmol) in $CH_2Cl_2$ (100 mL) at 0° C. was added pyridine (2.09 g, 26.5 mmol) followed by trifluoromethanesulfonic anhydride(3.68 g, 13.2 mmol). The solution was stirred 15 min and was allowed to warm to rt. After stirring 2 h the mixture was diluted with water, and was extracted with $CH_2Cl_2$. The combined organic layers were washed with water, brine and dried ($MgSO_4$). The solvent was removed under reduced pressure and the residue was chromatographed (silica gel, 7.5% EtOAc/hexanes) to give the triflate 3b (compound X, $R^3$=H, $R^6$=H) as a white solid (4.0 g, 88%); $^1H$ NMR ($CDCl_3$) δ 7.18 (m, 8H), 6.93 (m, 3H), 6.86 (dt, J=7.5, 1.1 Hz, 1H), 6.75 (dd, J=7.9, 1.6 Hz, 1H), 5.10 (s, 2H); $^{19}F$ NMR ($CDCl_3$) δ −73.15.

Example XIX

Preparation of intermediate 3-[4-(3-phenyl-2H-chromen-4-yl)-phenyl]-acrylic acid methyl ester 3c

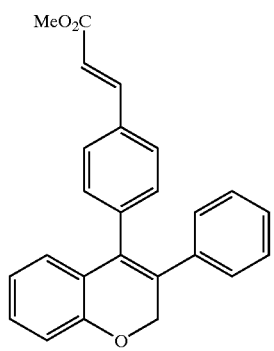

3c

Prepared from the Heck coupling of 3b and methyl acrylate by the general method described for example 2b. Yield (94%); APcI m/z: 410 (M+H+$CH_3CN^+$, 100%).

Example XX

Preparation of intermediate 3-[4-(3-phenyl-2H-chromen-4-yl)-phenyl]-acrylic acid 3d

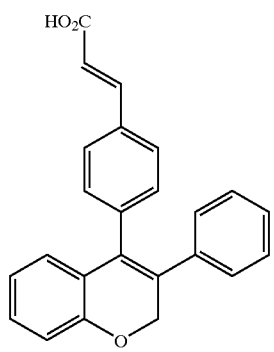

3d

Prepared from the saponification (hydrolysis) of ester 3c by the general method described for example 2e. Yield (86%); ESI m/z: 353 (M−H⁻, 100%).

Example XXI

Preparation of N-{3-[4-(3-phenyl-2H-chromen-4-yl)-phenyl]-acryloyl}-methanesulfonamide 3e

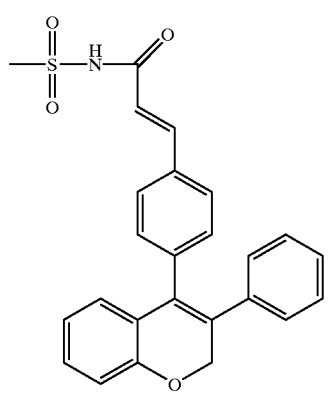

3e

Prepared from the coupling of 3d and methylsulfonamide by the method described in Procedure 1, Method A. Yield (35%); ESI m/z: 430 (M−H⁻, 100%).

Example XXII

Preparation of N-{3-[4-(3-phenyl-2H-chromen-4-yl)-phenyl]-acryloyl}-benzenesulfonamide 3f

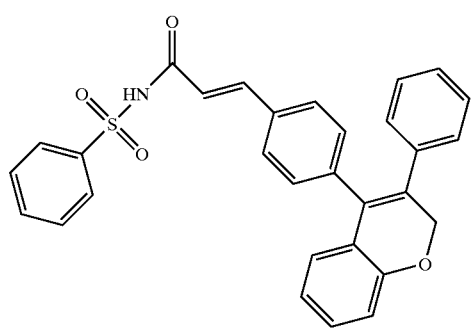

3f

Prepared from the coupling of 3d and benzene sulfonamide by the method described in Procedure 1, Method A. Yield (46%); ESI m/z: 492 (M−H⁻, 100%)

Example XXIII

Preparation of intermediate 3-[4-(1,2-diphenyl-but-1-enyl)-phenyl]-acrylonitrile 4b

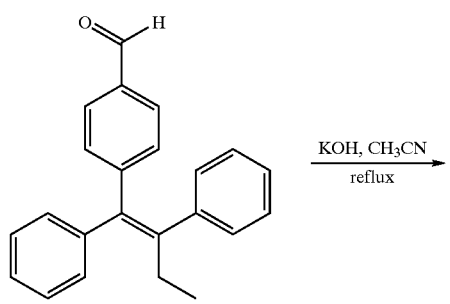

A suspension of potassium hydroxide (85%, 260 mg, 3.9 mmol) in CH₃CN (25 mL) was heated to reflux and (Z)-1,2-Diphenyl-1-(4-formylphenyl)-1-butene (4a, compound XII[1], R³=H, R⁶=H) (Willson *J. Med. Chem.* 1994, 37, 1550–1552) (1.0 g, 3.18 mmol) was added in portions. After refluxing 5 min the mixture was diluted with water and was extracted with EtOAc. The combined organic layers were washed with brine and dried (MgSO₄). The solvent was removed under reduced pressure and the residue was chromatographed (silica gel, 15% EtOAc/hexanes) to give the nitrile (4b, compound XIV, R³=H, R⁶=H) as a white solid (616 mg, 57%): ¹H NMR (CDCl₃) δ 7.39–7.07 (m, 13H), 6.91 (d, J=8.4 Hz, 2H), 5.69 (d, J=16.9 Hz, 1H), 2.48 (q, J=7.3 Hz, 2H), 0.94 (t, J=7.3 Hz, 3H); HRMS calcd. for C₂₅H₂₁N (M+H⁺) 335.1674; found 335.1679.

Example XXIV

Preparation of 5-{2-[4-(1,2-diphenyl-but-1-enyl)-phenyl]-vinyl}-1H-tetrazole 4c

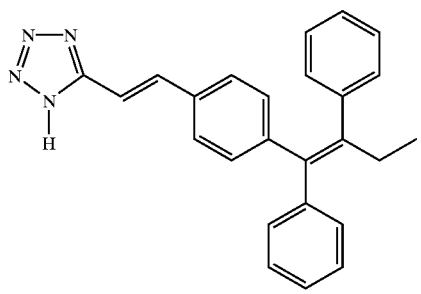

To a solution of aluminum chloride (1.82 g, 13.5 mmol) in THF (20 mL) at 0° C. was added sodium azide (1.77 g, 27 mmol) then nitrile (4b) (888 mg, 2.65 mmol). The mixture was stirred 10 min and was heated to reflux. After refluxing overnight the mixture was diluted with 1N HCl, and was extracted with EtOAc. The combined organic layers were washed with water, brine and were dried (MgSO₄). The solvent was removed under reduced pressure and the residue was chromatographed (silica gel, 10–20% methanol/CH₂Cl₂) to give the tetrazole (4c, compound XV, R³=H, R⁶=H) as a white solid (700 mg, 70%): ¹H NMR (CDCl₃) δ 7.63 (d, J=16.5 Hz, 1H), 7.39–7.11 (m, 12H), 6.98 (d, J=16.5 Hz, 1H), 6.91 (d, J=8.4 Hz, 2H), 2.48 (q, J=7.3 Hz, 2H), 0.94 (t, J=7.3 Hz, 3H); ESI m/z: 377 (M–H⁻, 100%).

Example XXV

Preparation of intermediate trifluoromethanesulfonic acid 4-(6-phenyl-8,9-dihydro-7H-benzocyclohepten-5-yl)-phenyl ester 5b

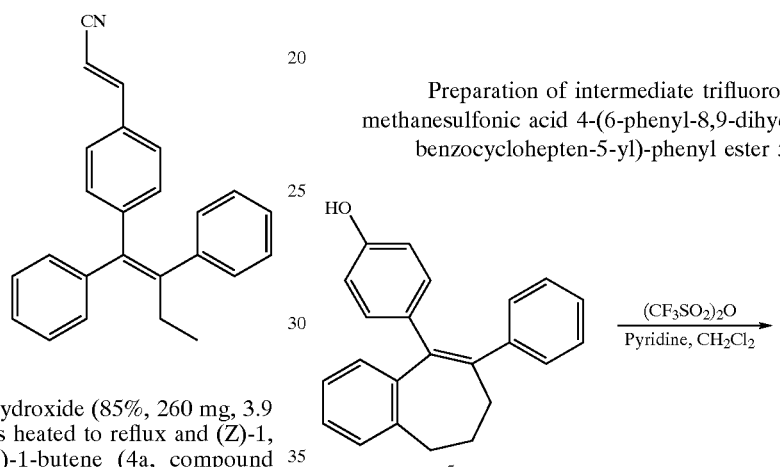

To a solution of 6,7-dihydro-8-phenyl-9-(4-hydroxyphenyl)-5H-benzocycloheptene (*J. Med. Chem.* 1986, 29, 2053–2059) (5a, compound XVI, R³=H, R⁶=H) (500 mg, 1.60 mmol) in CH₂Cl₂ (15 mL) at 0° C. was added pyridine (316 mg, 4.0 mmol) followed by trifluoromethanesulfonic anhydride(560 mg, 2.0 mmol). The solution was stirred 30 min and was diluted with water, and was extracted with CH₂Cl₂. The combined organic layers were washed with water, brine and dried (MgSO₄). The solvent was removed under reduced pressure and the residue was chromatographed (silica gel, 7.5% EtOAc/hexanes) to give the triflate (5b, compound XVII, R³=H, R⁶=H) as a white solid (665 mg, 94%): ¹H NMR (CDCl₃) δ 7.30–7.09 (m, 12H), 6.82 (dd, J=7.3, 1.5 Hz, 1H), 2.81 (t, J=7.0 Hz, 2H), 2.40 (t, J=7.0 Hz, 2H), 2.20 (m, 2H).

Example XXVI

Preparation of intermediate 3-[4-(6-phenyl-8,9-dihydro-7H-benzocyclohepten-5-yl)-phenyl]-acrylonitrile 5c

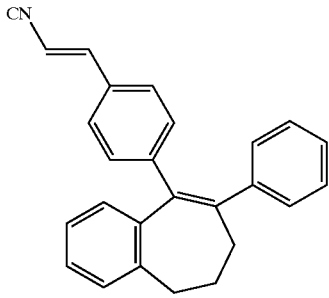

5c

To a solution of the triflate (5b) (560 mg, 1.25 mmol) in DMF (6 mL) was added acrylonitrile (2.10 g, 39.6 mmol), triethylamine (2.90 g, 28.6 mmol), and bis(triphenylphosphine)palladium(II) chloride (700 mg, 1.0 mmol). The mixture was placed in a pressure bottle and heated at 100° C. for 4 days. The solvent was removed under reduced pressure and the residue was chromatographed (silica gel, 15% EtOAc/hexanes) to give the nitrile (5c, compound XVIII, $R^3$=H, $R^6$=H) as a white solid (199 mg, 46%): $^1$H NMR (CDC1,) δ 7.30–7.13 (m, 11H), 6.94 (d, J=8.1 Hz, 2H), 6.82 (dd, J=7.3, 1.1 Hz, 1H), 5.75 (d, J=16.5 Hz, 1H), 2.81 (t, J=7.0 Hz, 2H), 2.40 (t, J=7.0 Hz, 2H), 2.19 (m, 2H)

Example XXVII

Preparation of 5-{2-[4-(6-phenyl-8,9-dihydro-7H-benzocyclohepten-5-yl)-phenyl]-vinyl}-1H-tetrazole 5d

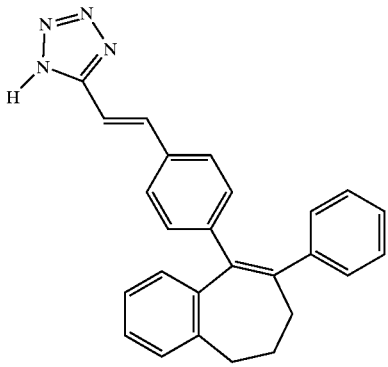

5d

To a solution of aluminum chloride (175 mg, 1.31 mmol) in THF (4 mL) at 0° C. was added sodium azide (170 mg, 2.61 mmol) then nitrile (5c) (133 mg, 0.38 mmol). The mixture was stirred 10 min and was heated to reflux. After refluxing 5 h the mixture was diluted with 1N HCl, and was extracted with EtOAc. The combined organic layers were washed with water and dried (MgSO$_4$). The solvent was removed under reduced pressure and the residue was chromatographed (silica gel, 10–20% methanol/CH$_2$Cl$_2$) to give the tetrazole (5d, compound XIX, $R^3$=H, $R^6$=H as a white solid (84 mg, 56%): $^1$H NMR (CDCl$_3$) δ 7.49 (d, J=16.8 Hz, 1H),7.34–7.06 (m, 12H), 6.91 (d, J=8.0 Hz, 2H), 6.79 (dd, J=7.3, 1.5 Hz, 1H), 2.84 (t, J=7.0 Hz, 2H), 2.38 (t, J=7.0 Hz, 2H), 2.16 (m, 2H); ESI m/z: 389 (M–H$^-$, 100%).

Example XXVIII

Preparation of N-{3-[4-(1,2-diphenyl-but-1-enyl)-phenyl]-acryloyl}-C,C,C-trifluoro-methanesulfonamide

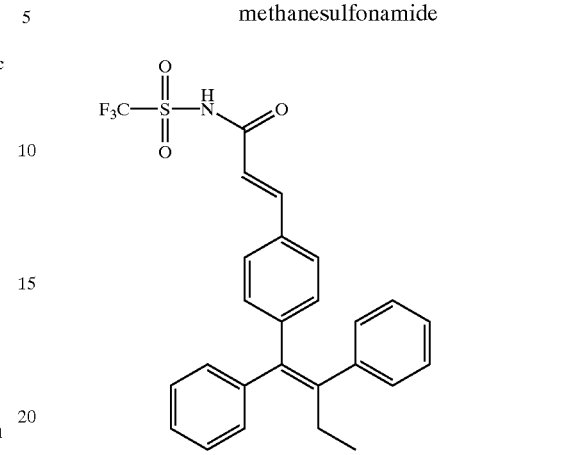

Procedure 1, Method B

Example 1e

To a solution of 1a (0.20 g, 0.564 mmol) in CH$_2$cl$_2$ (3 mL) were added trifluoromethanesulfonamide (0.236 g, 1.58 mmol), 4-dimethylaminopyridine (0.104 g, 0.851 mmol), and 1-[3-(dimethylamino)propyl]-3-ethylcarbodiimide hydrochloride (0.162 g, 0.851 mmol). After stirring at room temperature for 24 hours, PS-Trisamine resin (0.600 mg) was added and stirring continued for one hour. The resin was collected by vacuum filtration and washed with 5% MeOH in CH$_2$Cl$_2$. The resin was treated with 5% TFA in CH$_2$Cl$_2$ (5 mL) and collected by vacuum filtration. The filtrate was concentrated in vacuo to yield compound 1 as a pale yellow solid (0.041 mg, 15%): $^1$H NMR (DMSO-d$_6$) δ 7.38–7.09 (m, 13H), 6.79 (d, J=8.4 Hz, 2H), 6.29 (d, J=15.8 Hz, 1H), 2.35 (q, J=7.4 Hz), 0.82 (t, J=7.4 Hz, 3H); ApcI m/z=484.2 (M–H$^-$).

Example XXIX

Preparation of N-{3-[4-(1,2-diphenyl-but-1-enyl)-phenyl]-acryloyl}-2-nitro-benzenesulfonamide

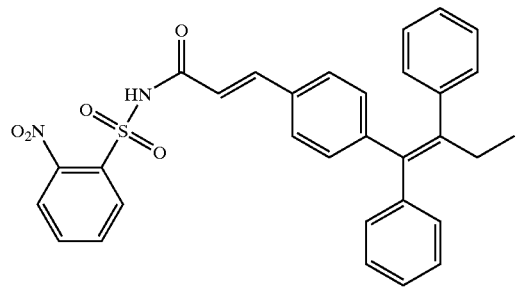

1f

Example 1f

Prepared from the coupling of 1a and 2-nitrobenzenesulfonamide by the method described in Procedure 1, Method B. Yield (22%); $^1$H NMR (d$_6$-DMSO) δ 8.18 (d, J=5.2 Hz, 1H), 7.99 (d, J=5.9 Hz, 1H), 7.94–7.84

(m, 2H), 7.44–7.08 (m, 13H), 6.86 (d, J=8.1 Hz, 2H), 6.50 (d, J=15.7 Hz, 1H), 2.36 (q, J=7.4 Hz, 2H), 0.82 (t, J=7.4 Hz, 3H); APcI m/z: 539 (M+H$^+$).

Example XXX

Preparation N-{3-[4-(1,2-diphenyl-but-1-enyl)-phenyl]-acryloyl}-3-nitro-benzenesulfonamide

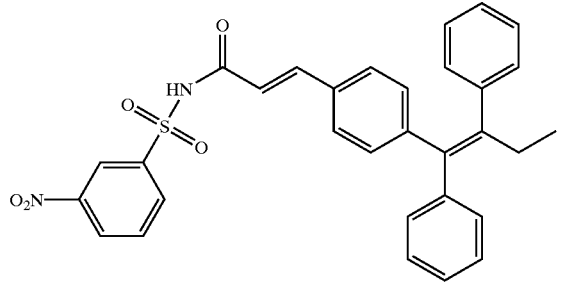

Example 1g

Prepared from the coupling of 1a and 3-nitrobenzenesulfonamide by the method described in Procedure 1, Method A. Yield (14%); $^1$H NMR (d$_6$-DMSO) δ 8.59 (t, J=2.2 Hz, 1H), 8.47 (d, J=7.0 Hz, 1H), 8.30 (d, J=7.7 Hz, 1H) 7.87 (t, J=8.1 Hz, 1H), 7.38–7.07 (m, 13H), 6.83 (d, J=8.4 Hz, 2H), 6.38 (d, J=15.7 Hz, 1H), 2.35 (q, J=7.4 Hz, 2H), 0.81 (t, J=7.4 Hz, 3H); APcI m/z: 537 (M–H$^-$).

Example XXXI

Preparation N-{3-[4-(1,2-diphenyl-but-1-enyl)-phenyl]-acryloyl}-4-nitro-benzenesulfonamide

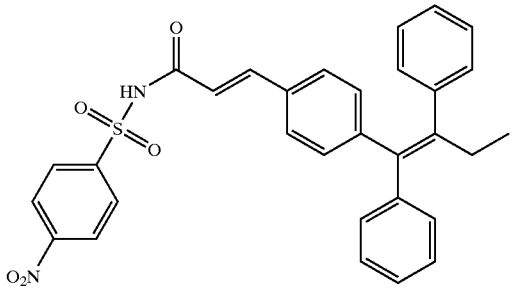

Example 1h

Prepared from the coupling of 1a and 4-nitrobenzenesulfonamide by the method described in Procedure 1, Method A. Yield (32%); $^1$H NMR (d$_6$-DMSO) δ 8.33 (d, J=8.8 Hz, 2H), 8.08 (d, J=8.8 Hz, 2H), 7.38–7.07 (m, 13H), 6.82 (d, J=8.0 Hz, 2H), 6.35 (d, J=15.7 Hz, 1H), 2.35 (q, J=7.3 Hz, 2H), 0.81 (t, J=7.3 Hz, 3H); APcI m/z: 538 (M$^+$).

Example XXXII

Preparation of N-{3-[4-(1,2-diphenyl-but-1-enyl)-phenyl]-acryloyl}-2-trifluoromethyl-benzenesulfonamide

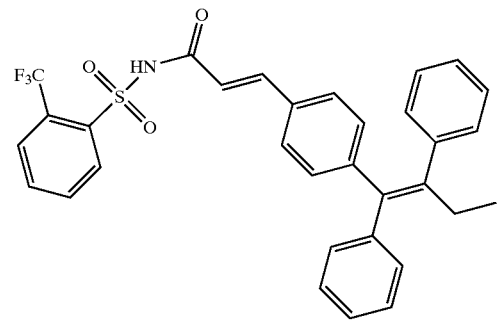

Example 1i

Prepared from the coupling of 1a and 2-(trifluoromethyl) benzenesulfonamide (Synlett, 1997, 375) by the method described in Procedure 1, Method B. Yield (14%); $^1$H NMR (d$_6$-DMSO) δ 12.49 (br s, 1H), 7.98–7.90 (m, 3H), 7.39–7.08 (m, 13H), 6.85 (d, J=8.0 Hz, 2H), 6.47 (d, J=15.7 Hz, 1H), 2.36 (q, J=7.3 Hz, 2H), 0.82 (t, J=7.3 Hz, 3H); APcI m/z: 562 (M+H$^+$).

Example XXXIII

Preparation of N-{3-[4-(1,2-diphenyl-but-1-enyl)-phenyl]-acryloyl}-3-trifluoromethyl-benzenesulfonamide

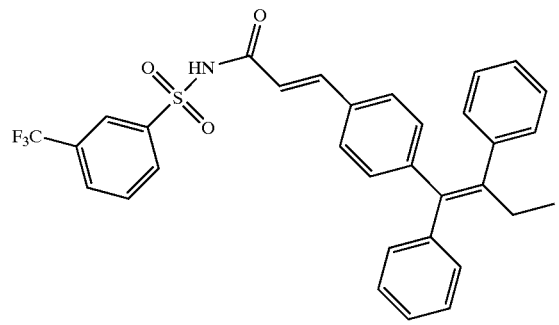

Example 1j

Prepared from the coupling of 1a and 3-(trifluoromethyl) benzenesulfonamide (Synlett, 1997, 375) by the method described in Procedure 1, Method B. Yield (35%); $^1$H NMR (d$_6$-DMSO) δ 8.22–8.08 (m, 3H), 7.86 (t, J=7.7 Hz, 1H), 7.42–7.07 (m, 13H), 6.84 (d, J=8.0 Hz, 2H), 6.40 (d, J=15.7 Hz, 1H), 2.35 (q, J=7.3 Hz, 2H), 0.82 (t, J=7.3 Hz, 3H); APcI m/z: 562 (M+H$^+$).

Example XXXIV

Preparation of N-{3-[4-(1,2-diphenyl-but-1-enyl)-phenyl]-acryloyl}-4-trifluoromethyl-benzenesulfonamide

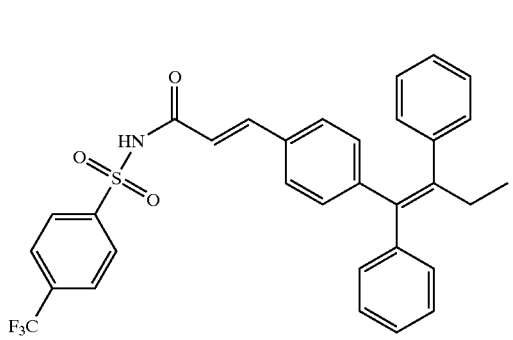

Example 1k

Prepared from the coupling of 1a and 4-(trifluoromethyl)benzenesulfonamide (Synlett, 1997, 375) by the method described in Procedure 1, Method B. Yield (18%); $^1$H NMR ($d_6$-DMSO) δ 12.46 (br s, 1H), 8.11 (d, J=8.5 Hz, 2H), 7.99 (d, J=8.5 Hz, 2H), 7.40–7.07 (m, 13H), 6.84 (d, J=8.1 Hz, 2H), 6.40 (d, J=15.7 Hz, 1H), 2.35 (q, J=7.3 Hz, 2H), 0.81 (t, J=7.3 Hz, 3H); APcI m/z: 562 (M+H$^+$).

Example XXXV

Preparation of 4-cyano-N-{3-[4-(1,2-diphenyl-but-1-enyl)-phenyl]-acryloyl}-benzenesulfonamide

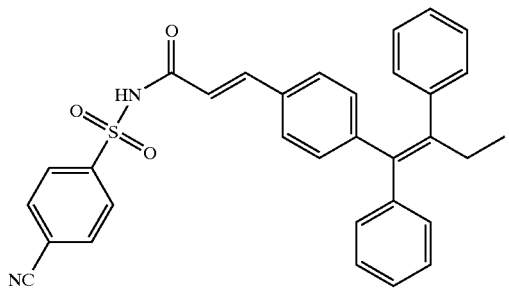

Example 1l

Prepared from the coupling of 1a and 4-cyanobenzenesulfonamide by the method described in Procedure 1, Method B. Yield (21%); $^1$H NMR ($d_6$-DMSO) δ 8.09–8.03 (m, 4H), 7.94 (d, J=8.0 Hz, 1H), 7.40–7.07 (m, 12H), 6.84 (d, J=8.0 Hz, 2H), 6.40 (d, J=15.7 Hz, 1H), 2.35 (q, J=7.4 Hz, 2H), 0.82 (t, J=7.4 Hz, 3H); APcI m/z: 519 (M+H$^+$).

Example XXXVI

Preparation of 2-chloro-N-{3-[4-(1,2-diphenyl-but-1-enyl)-phenyl]-acryloyl}-benzenesulfonamide

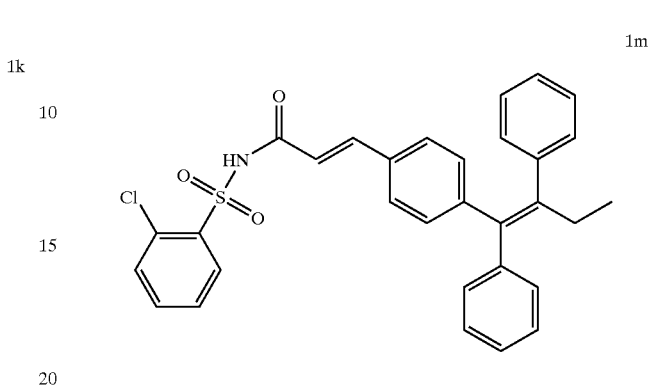

Example 1m

Prepared from the coupling of 1a and 2-chlorobenzenesulfonamide by the method described in Procedure 1, Method B. Yield (19%); $^1$H NMR ($d_6$-DMSO) δ 12.56 (s, 1H), 8.09 (d, J=7.7 Hz, 1H), 7.69–7.53 (m, 3H), 7.39–7.08 (m, 13H), 6.85 (d, J=8.1 Hz, 2H), 6.47 (d, J=15.8 Hz, 1H), 2.36 (q, J=7.3 Hz, 2H), 0.82 (t, J=7.3 Hz, 3H); APcI m/z: 528 (M+H$^+$).

Example XXXVII

Preparation of 3-chloro-N-{3-[4-(1,2-diphenyl-but-1-enyl)-phenyl]-acryloyl}-benzenesulfonamide

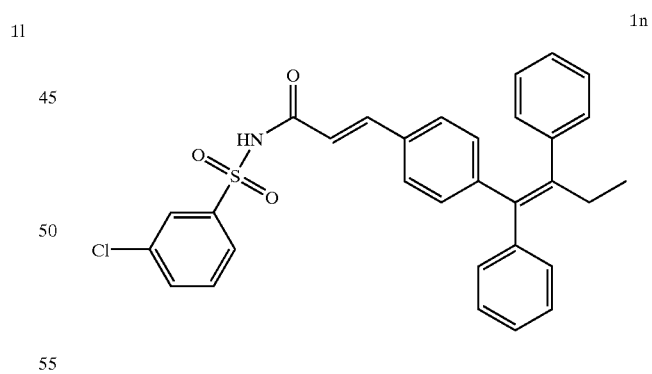

Example 1n

Prepared from the coupling of 1a and 3-chlorobenzenesulfonamide by the method described in Procedure 1, Method B. Yield (25%); $^1$H NMR ($d_6$-DMSO) δ 12.36 (s, 1H), 7.88–7.76 (m, 3H), 7.63 (t, J=8.1 Hz, 1H), 7.42–7.07 (m, 13H), 6.84 (d, J=8.0 Hz, 2H), 6.40 (d, J=15.7 Hz, 1H), 2.36 (q, J=7.3 Hz, 2H), 0.82 (t, J=7.3 Hz, 3H); APcI m/z: 527 (M−H$^-$).

Example XXXVIII

Preparation of 4-chloro-N-{3-[4-(1,2-diphenyl-but-1-enyl)-phenyl]-acryloyl}-benzenesulfonamide

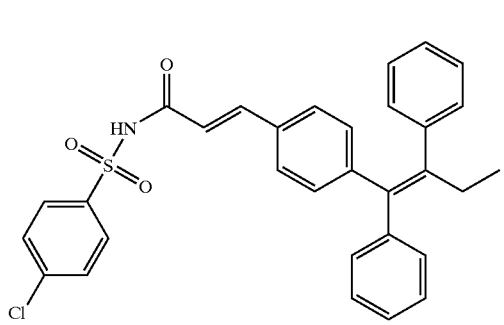

Example 1o

Prepared from the coupling of 1a and 4-chlorobenzenesulfonamide by the method described in Procedure 1, Method B. Yield (22%); $^1$H NMR ($d_6$-DMSO) δ 12.31 (br s, 1H), 7.90 (d, J=8.4 Hz, 2H), 7.66 (d, J=8.4 Hz, 2H), 7.39–7.07 (m, 13H), 6.84 (d, J=8.0 Hz, 2H), 6.40 (d, J=15.7 Hz, 1H), 2.35 (q, J=7.4 Hz, 2H), 0.82 (t, J=7.4 Hz, 3H); APcI m/z: 527 (M–H$^-$).

Example XXXIX

Preparation of N-{3-[4-(1,2-diphenyl-but-1-enyl)-phenyl]-acryloyl}-2-methyl-benzenesulfonamide

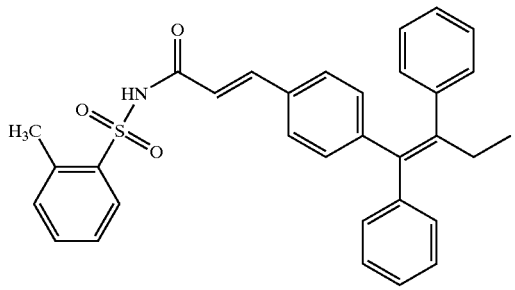

Example 1p

Prepared from the coupling of 1a and O-toluenesulfonamide by the method described in Procedure 1, Method B. Yield (37%); $^1$H NMR (CD$_3$OD) δ 11.63 (br s, 1H), 7.54 (d, J=15.7 Hz, 2H), 7.39–7.09 (m, 15H), 6.87 (d, J=8.0 Hz, 2H), 6.81 (s, 1H), 6.41 (d, J=15.7 Hz, 1H), 3.02–2.73 (s, 3H), 2.37 (q, J=7.3 Hz, 2H), 0.83 (t, J=7.3 Hz, 3H); APcI m/z: 508 (M+H$^+$).

Example XL

Preparation of N-{3-[4-(1,2-diphenyl-but-1-enyl)-phenyl]-acryloyl}-3-methyl-benzenesulfonamide

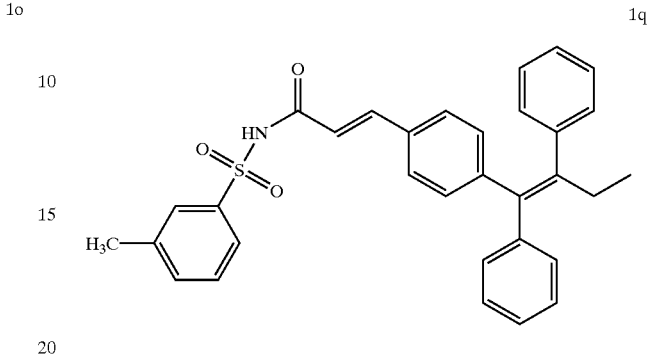

Example 1q

Prepared from the coupling of 1a and m-toluenesulfonamide (Synlett, 1997, 375) by the method described in Procedure 1, Method B. Yield (24%); $^1$H NMR (CDCl$_3$) δ 7.86 (m, 2H), 7.50 (d, J=15.7 Hz, 1H), 7.42–7.07 (m, 14H), 6.86 (d, J=8.4 Hz, 2H), 6.27 (d, J=15.7 Hz, 1H), 2.47 (q, J=7.3 Hz, 2H), 2.41 (s, 3H), 0.93 (t, J=7.3 Hz, 3H); APcI m/z: 508 (M+H$^+$).

Example XLI

Preparation of N-{3-[4-(1,2-diphenyl-but-1-enyl)-phenyl]-acryloyl}-4-methyl-benzenesulfonamide

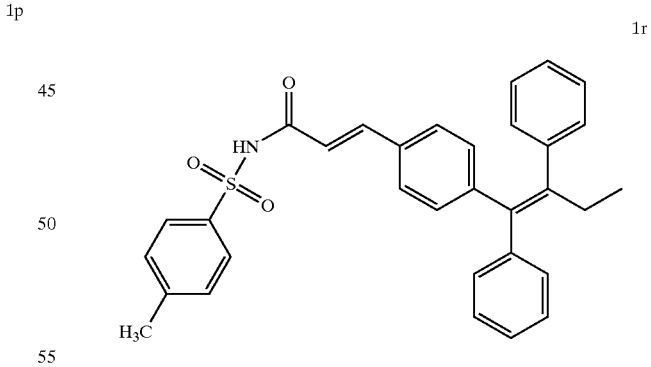

Example 1r

Prepared from the coupling of 1a and p-toluenesulfonamide by the method described in Procedure 1, Method B. Yield (42%); $^1$H NMR (CD$_3$OD) δ 7.87 (d, J=8.2 Hz, 2H), 7.37–7.08 (m, 15H), 6.87 (d, J=8.2 Hz, 2H), 6.32 (d, J=15.7 Hz, 1H), 2.44 (q, J=7.4 Hz, 2H), 2.40 (s, 3H), 0.89 (t, J=7.3 Hz, 3H); APcI m/z: 508 (M+H$^+$).

Example XLII

Preparation of 4-{3-[4-(1,2-diphenyl-but-1-enyl)-phenyl]-acryloylsulfamoyl}-benzoic acid methyl ester 1s

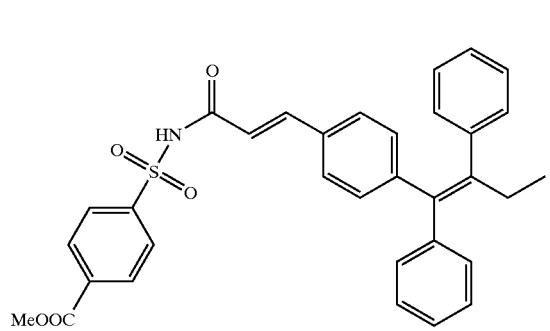

Example 1s

Prepared from the coupling of 1a and p-carboxybenzenesulfonamide methyl ester (Synlett, 1997, 375) by the method described in Procedure 1, Method B. Yield (25%); $^1$H NMR (d$_6$-DMSO) δ 8.13 (d, J=8.8 Hz, 2H), 8.03 (d, J=8.8 Hz, 2H), 7.39–7.07 (m, 13H), 6.84 (d, J=8.4 Hz, 2H), 6.40 (d, J=15.7 Hz, 1H), 3.86 (s, 3H), 2.36 (q, J=7.3 Hz, 2H), 2.41 (s, 3H), 0.82 (t, J=7.3 Hz, 3H); APcI m/z: 552 (M+H$^+$).

Example XLIII

Preparation of N-{3-[4-(1,2-diphenyl-but-1-enyl)-phenyl]-acryloyl}-4-methoxy-benzenesulfonamide 1t

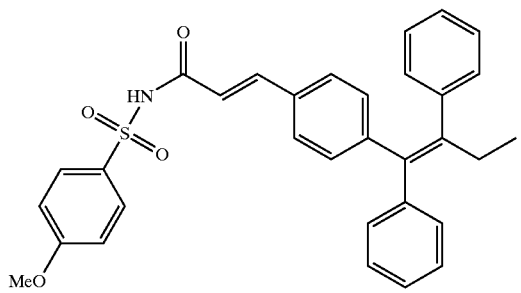

Example 1t

Prepared from the coupling of 1a and 4-methoxybenzenesulfonamide by the method described in Procedure 1, Method B. Yield (24%); $^1$H NMR (d$_6$-DMSO) δ 12.04 (br s, 1H), 7.83 (d, J=8.8 Hz, 2H), 7.38–7.07 (m, 15H), 6.84 (d, J=8.0 Hz, 2H), 6.39 (d, J=15.7 Hz, 1H), 3.80 (s, 3H), 2.35 (q, J=7.3 Hz, 2H), 0.82 (t, J=7.3 Hz, 3H); APcI m/z: 525 (M+H$^+$).

Example XLIV

Preparation of N-{3-[4-(1,2-diphenyl-but-1-enyl)-phenyl]-acryloyl}-3-methoxy-benzenesulfonamide 1u

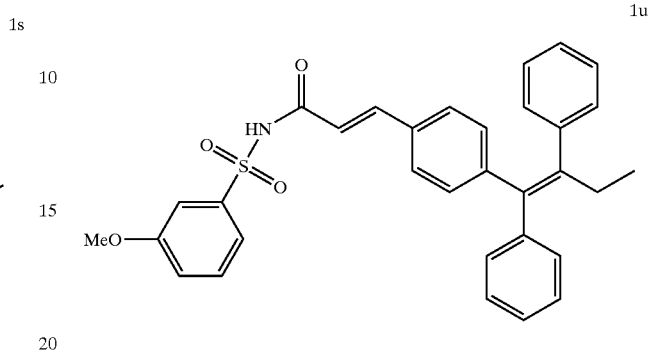

Example 1u

Prepared from the coupling of 1a and 3-methoxybenzenesulfonamide (Synlett, 1997, 375) by the method described in Procedure 1, Method B. Yield (27%); $^1$H NMR (d$_6$-DMSO) δ 12.18 (br s, 1H), 7.53–7.07 (m, 17H), 6.84 (d, J=8.0 Hz, 2H), 6.40 (d, J=15.7 Hz, 1H), 3.78 (s, 3H), 2.35 (q, J=7.4 Hz, 2H), 0.82 (t, J=7.4 Hz, 3H); APcI m/z: 522 (M−H$^−$).

Example XLV

Preparation of N-{3-[4-(1,2-diphenyl-but-1-enyl)-phenyl]-acryloyl}-4-hydroxy-benzenesulfonamide 1v

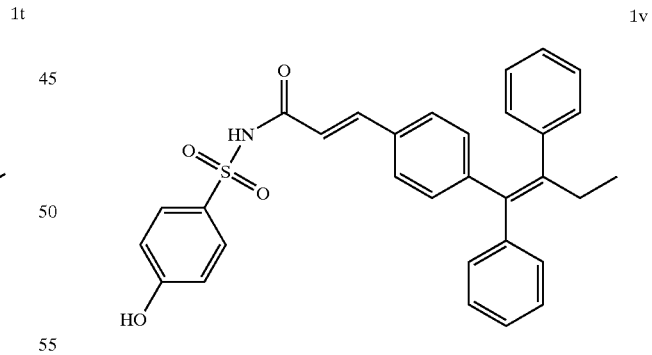

Example 1v

Prepared from 1t by treating with boron tribromide (3 eq) in CH$_2$Cl$_2$ at room temperature. Yield (29%); $^1$H NMR (d$_6$-DMSO) δ 11.95 (br s, 1H), 10.57 (s, 1H), 7.71 (d, J=8.8 Hz, 2H), 7.38–7.07 (m, 13H), 6.85 (t, J=8.8 Hz, 4H), 6.38 (d, J=15.7 Hz, 1H), 2.36 (q, J=7.4 Hz, 2H), 0.82 (t, J=7.4 Hz, 3H); APcI m/z: 510 (M+H$^+$).

Example XLVI

Preparation of N-{3-[4-(1,2-diphenyl-but-1-enyl)-phenyl]-acryloyl}-3-hydroxy-benzenesulfonamide

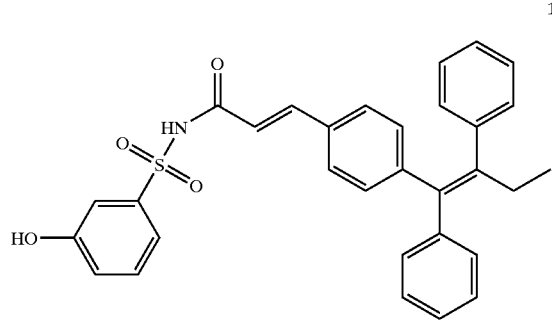

Example 1w

Prepared from 1u by treating with boron tribromide (3 eq) in CH$_2$Cl$_2$ at room temperature. Yield (57%); $^1$H NMR (d$_6$-DMSO) δ 12.15 (br s, 1H), 10.19 (s, 1H), 7.41–7.02 (m, 17H), 6.86 (d, J=8.0 Hz, 2H), 6.42 (d, J=15.7 Hz, 1H), 2.37 (q, J=7.4 Hz, 2H), 0.83 (t, J=7.4 Hz, 3H); APcI m/z: 510 (M+H$^+$).

Example XLVII

Preparation of 3-chloro-propane-1-sulfonic acid {3-[4-(1,2-diphenyl-but-1-enyl)-phenyl]-acryloyl}-amide

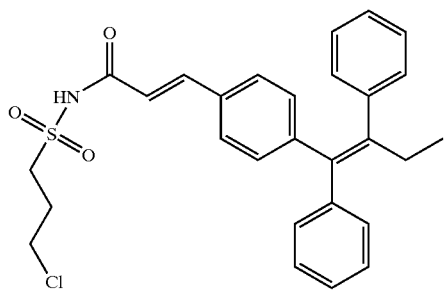

Example 1x

Prepared from the coupling of 1a and 3-chloropropanesulfonamide (Synlett, 1997, 375) by the method described in Procedure 1, Method A. Yield (80%); $^1$H NMR (d$_6$-DMSO) δ 11.82 (br s, 1H), 7.48 (d, J=15.7 Hz, 1H), 7.40–7.09 (m, 12H), 6.87 (d, J=8.4 Hz, 2H), 6.46 (d, J=15.7 Hz, 1H), 3.71 (t, 2H), 3.52 (t, 2H), 2.37 (q, J=7.3 Hz, 2H), 2.07 (p, 2H), 0.83 (t, J=7.3 Hz, 3H); APcI m/z: 492 (M−H$^-$).

Example XLVIII

Preparation of (4-{3-[4-(1,2-diphenyl-but-1-enyl)-phenyl]-acryloylsulfamoyl}-phenyl)-carbamic acid tert-butyl ester

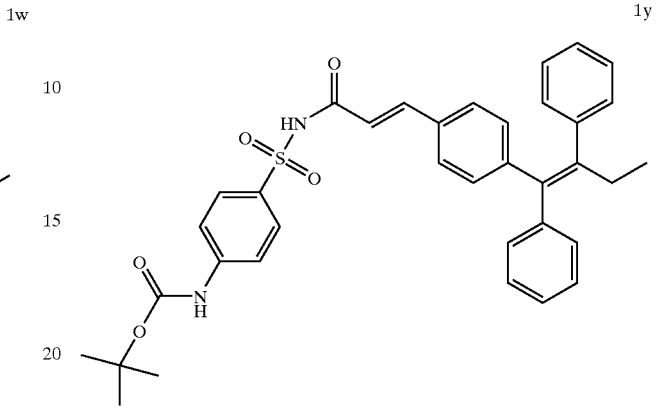

Example 1y

Prepared from the coupling of 1a and 4-BOC sulfanilamide (Heterocycles, 1996, 2741; Synlett, 1997, 375) by the method described in Procedure 1, Method A. Yield (67%); $^1$H NMR (d$_6$-DMSO) δ 12.02 (br s, 1H), 9.86 (s, 1H), 7.78 (d, J=8.8 Hz, 2H), 7.60 (d, J=8.8 Hz, 2H), 7.38–7.08 (m, 13H), 6.83 (d, J=8.4 Hz, 2H), 6.38 (d, J=15.7 Hz, 1H), 2.36 (q, J=7.3 Hz, 2H), 1.44 (s, 9H), 0.82 (t, J=7.3 Hz, 3H); APcI m/z: 607 (M−H$^-$).

Example XLIX

Preparation of 3-Piperidin-1-yl-propane-1-sulfonic acid {3-[4-(1,2-diphenyl-but-1-enyl)-phenyl]-acryloyl}-amide

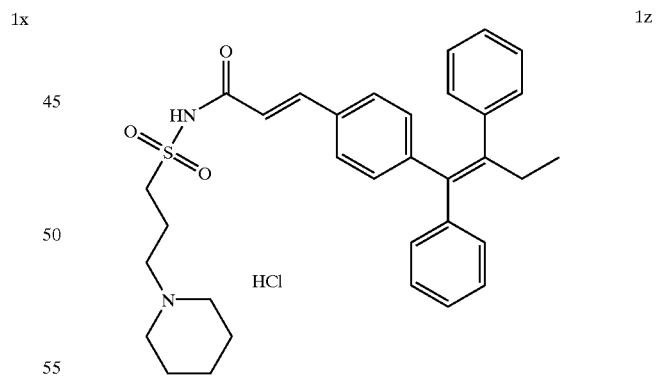

Example 1z

Prepared from the coupling of 1x and piperidine (15 eq) in tetrahydrofuran at reflux. The product precipitated from a mixture of ethyl acetate and 1N HCl as the HCl salt. Yield (60%); $^1$H NMR (d$_6$-DMSO) δ 11.90 (br s, 1H), 7.47 (d, J=15.7 Hz, 1H), 7.40–7.09 (m, 12H), 6.87 (d, J=7.7 Hz, 2H), 6.53 (d, J=15.7 Hz, 1H), 3.08 (br, 2H), 2.95 (br, 1H), 2.81 (br, 2H), 2.37 (q, J=7.3 Hz, 2H), 2.08 (br, 2H), 1.71 (br, 6H), 1.62 (br, 1H), 0.83 (t, J=7.3 Hz, 3H); APcI m/z: 541 (M−H$^-$).

Example L

Preparation of 4-amino-N-{3-[4-(1,2-diphenyl-but-1-enyl)-phenyl]-acryloyl}-benzenesulfonamide

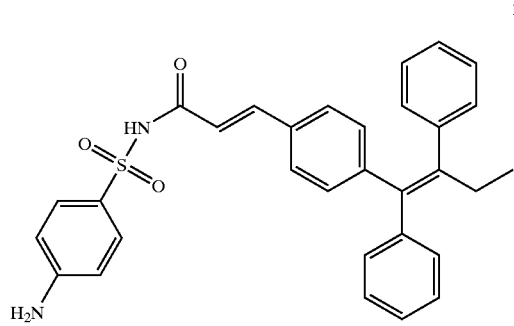

Example 1aa

Prepared from the treatment of 1y with trifluoroacetic acid (50% in CH$_2$Cl$_2$). Yield (92%); $^1$H NMR (d$_6$-DMSO) δ 11.71 (br s, 1H), 7.51 (d, J=8.7 Hz, 2H), 7.38–7.07 (m, 13H), 6.83 (d, J=8.1 Hz, 2H), 6.55 (d, J=8.7 Hz, 2H), 6.37 (d, J=15.7 Hz, 1H), 2.35 (q, J=7.4 Hz, 2H), 1.44 (s, 9H), 0.82 (t, J=7.3 Hz, 3H); APcI m/z: 507 (M−H$^-$).

Example LI

Preparation of Ethanesulfonic Acid {3-[4-(1,2-diphenyl-but-1-enyl)-phenyl]-acryloyl}-amide

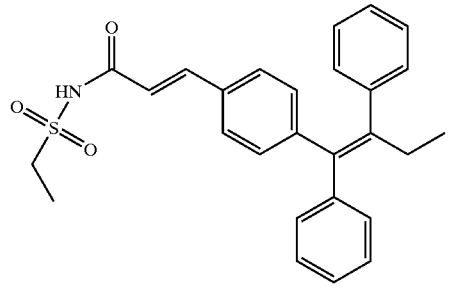

Example 1y

Prepared from the coupling of 1a and ethanesulfonamide (Synlett, 1997, 375) by the method described in Procedure 1, Method B. Yield (25%); $^1$H NMR (d$_6$-DMSO) δ 11.67 (br s, 1H), 7.47 (d, J=15.7 Hz, 1H), 7.40–7.09 (m, 12H), 6.86 (d, J=8.4 Hz, 2H), 6.47 (d, J=15.7 Hz, 1H), 3.37 (q, J=7.4 Hz, 2H), 2.36 (q, J=7.3 Hz, 2H), 1.16 (t, J=7.3 Hz, 3H), 0.83 (t, J=7.3 Hz, 3H); APcI m/z: 444 (M−H$^-$).

Example LII

Preparation of 4-{3-[4-(1,2-diphenyl-but-1-enyl)-phenyl]-acryloylsulfamoyl}-N,N-dimethyl-benzamide

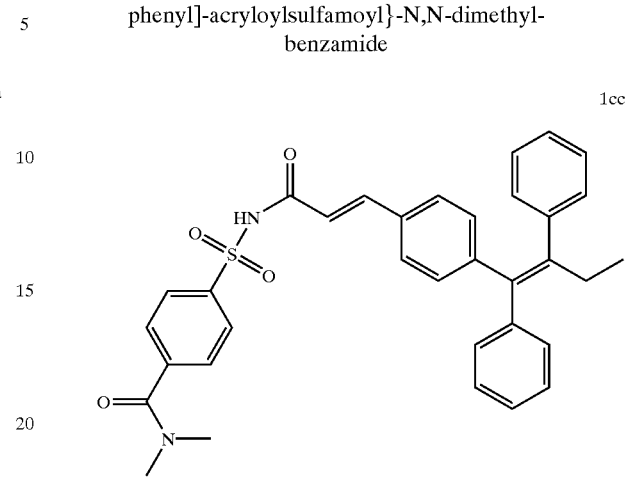

Example 1cc

Prepared from the coupling of 1aa with N,N-dimethylglycine (2.8 eq) using 4-dimethylaminopyridine (1.5 eq) and 1-[3-(dimethylamino)propyl]-3-ethylcarbodiimide hydrochloride (1.5 eq) in CH$_2$Cl$_2$ at room temperature. The product was isolated as the hydrochloride salt. Yield (28%); $^1$H NMR (d$_6$-DMSO) δ 10.26 (br s, 1H), 7.76 (q, J=8.5 Hz, 4H), 7.38–7.08 (m, 13H), 6.81 (d, J=8.1 Hz, 2H), 6.34 (d, J=15.7 Hz, 1H), 3.35 (br s, 2H), 2.39–2.35 (m, 8H), 0.82 (t, J=7.3 Hz, 3H); APcI m/z: 594 (M+H$^+$).

Example LIII

Preparation of propane-2-sulfonic acid {3-[4-(1,2-diphenyl-but-1-enyl)-phenyl]-acryloyl}-amide

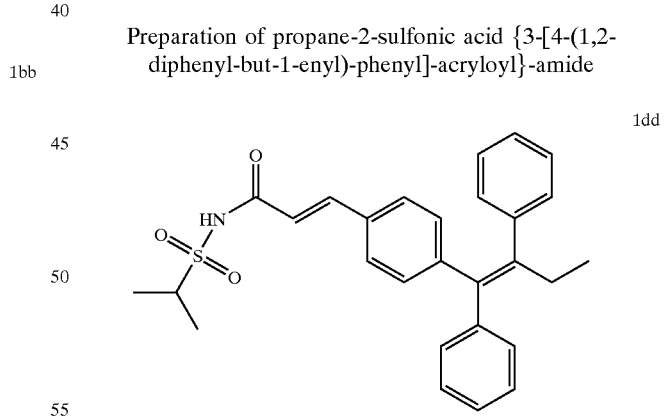

Example 1dd

Prepared from the coupling of 1a and isopropylsulfonamide (Synlett, 1997, 375) by the method described in Procedure 1, Method B. Yield (13%); $^1$H NMR (d$_6$-DMSO) δ 11.60 (br s, 1H), 7.46 (d, J=15.7 Hz, 1H), 7.40–7.09 (m, 12H), 6.86 (d, J=8.1 Hz, 2H), 6.48 (d, J=15.7 Hz, 1H), 3.64 (m, 1H), 2.37 (q, J=7.3 Hz, 2H), 1.23 (d, J=7.0 Hz, 6H), 0.83 (t, J=7.3 Hz, 3H); APcI m/z: 460 (M+H$^+$).

Example LIV

Preparation of N-{3-[4-(1,2-diphenyl-but-1-enyl)-phenyl]-acryloyl}-(4-fluoro-phenyl)-methanesulfonamide

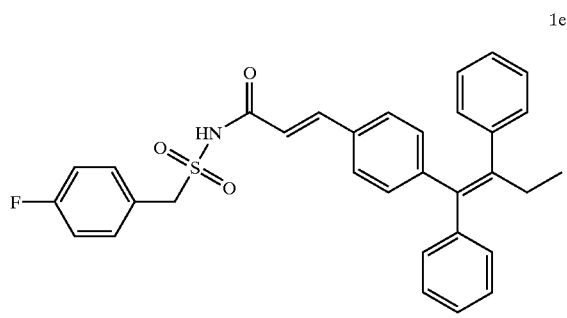

1ee

Example 1ee

Prepared from the coupling of 1a and [(4-fluorophenyl)methyl]sulfonamide (Synlett, 1997, 375) by the method described in Procedure 1, Method B. Yield (32%); $^1$H NMR (d$_6$-DMSO) δ 11.63 (br s, 1H), 7.53 (d, J=15.7 Hz, 1H), 7.40–7.10 (m, 16H), 6.87 (d, J=8.1 Hz, 2H), 6.41 (d, J=15.7 Hz, 1H), 4.72 (s, 2H), 2.37 (q, J=7.4 Hz, 2H), 0.83 (t, J=7.4 Hz, 3H); APcI m/z: 526 (M+H$^+$).

Example LV

Preparation of 4-{3-[4-(1,2-diphenyl-but-1-enyl)-phenyl]-acryloylsulfamoyl}-benzoic acid

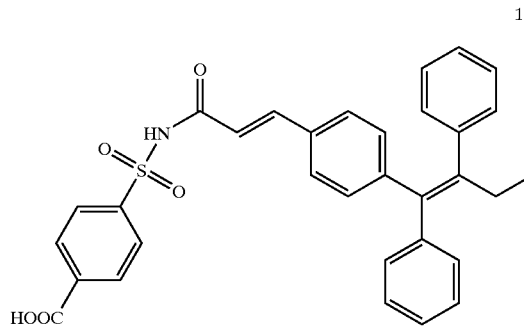

1ff

Example 1ff

Prepared from the hydrolysis of 1s using 4N aq sodium hydroxide (2 eq) in 4:1 dioxane/methanol at room temperature. Yield (82%); $^1$H NMR (d$_6$-DMSO) δ 13.48 (br s, 1H), 12.36 (br s, 1H), 8.10 (d, J=8.0 Hz, 2H), 8.02 (d, J=8.0 Hz, 2H), 7.39–7.07 (m, 13H), 6.84 (d, J=8.1 Hz, 2H), 6.41 (d, J=15.7 Hz, 1H), 2.35 (q, J=7.7 Hz, 2H), 0.82 (t, J=7.7 Hz, 3H); APcI m/z: 538 (M+H$^+$).

Example LVI

Preparation of N-(4-{3-[4-(1,2-diphenyl-but-1-enyl)-phenyl]-acryloylsulfamoyl}-phenyl)-acetamide

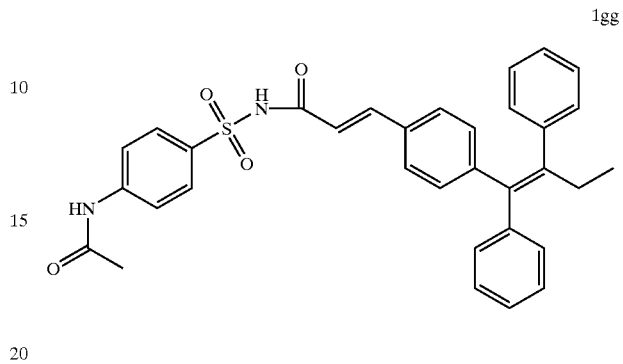

1gg

Example 1gg

Prepared by the acylation of 1aa with acetyl chloride (1.3 eq) in refluxing tetrahydrofuran using triethylamine (2.6 eq) as base. Yield (81%); $^1$H NMR (d$_6$-DMSO) δ 12.06 (br s, 1H), 10.35 (br s, 1H), 7.82 (d, J=9.0 Hz, 2H), 7.73 (d, J=9.0 Hz, 2H), 7.38–7.07 (m, 13H), 6.84 (d, J=8.1 Hz, 2H), 6.39 (d, J=15.7 Hz, 1H), 2.35 (q, J=7.4 Hz, 2H), 2.04 (s, 3H), 0.82 (t, J=7.4 Hz, 3H); APcI m/z: 551 (M+H$^+$).

Example LVII

Preparation of 2,2,2-trifluoro-ethanesulfonic acid {3-[4-(1,2-diphenyl-but-1-enyl)-phenyl]-acryloyl}-amide

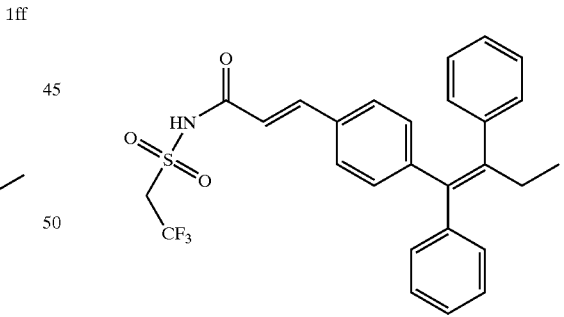

1hh

Example 1hh

Prepared from the coupling of 1a and 2,2,2-trifluoroethanesulfonamide (Synlett, 1997, 375) by the method described in Procedure 1, Method A. Yield (34%); $^1$H NMR (d$_6$-DMSO) δ 7.39–7.01 (m, 13H), 6.83 (d, J=8.1 Hz, 2H), 6.40 (d, J=15.7 Hz, 1H), 2.85 (s, 1H), 2.69 (s, 1H), 2.36 (q, J=7.3 Hz, 2H), 0.83 (t, J=7.3 Hz, 3H); ESI m/z: 498 (M−H$^-$).

Example LVIII

Preparation of thiophene-2-sulfonic acid {3-[4-(1,2-diphenyl-but-1-enyl)-phenyl]-acryloyl}-amide

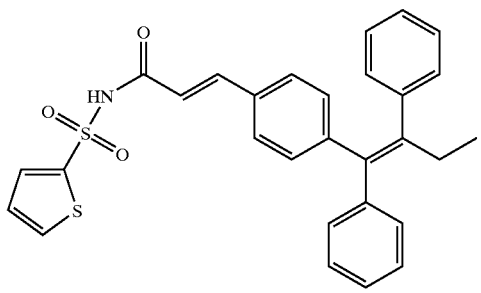

Example 1ii

Prepared from the coupling of 1a and 2-thiophenesulfonamide (Synlett, 1997, 375) by the method described in Procedure 1, Method A. Yield (27%); $^1$H NMR ($d_6$-DMSO) δ 12.34 (br s, 1H), 7.99 (m, 1H), 7.76 (m, 1H), 7.39–7.08 (m, 14H), 6.85 (d, J=8.4 Hz, 2H), 6.41 (d, J=15.7 Hz, 1H), 2.36 (q, J=7.3 Hz, 2H), 0.82 (t, J=7.3 Hz, 3H); APcI m/z: 500 (M+H$^+$).

Example LIX

Preparation of N-{3-[4-(1,2-diphenyl-but-1-enyl)-phenyl]-acryloyl}-C-(4-trifluoromethyl-phenyl)-methanesulfonamide

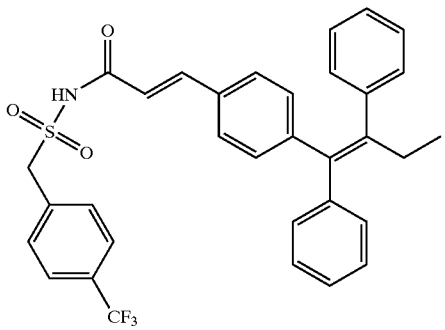

Example 1jj

Prepared from the coupling of 1a and [(4-trifluoromethylphenyl)methyl]sulfonamide (Synlett, 1997, 375) by the method described in Procedure 1, Method B. Yield (11%); $^1$H NMR ($d_6$-DMSO) δ 11.69 (br s, 1H), 7.74 (d, J=8.0 Hz, 2H), 7.57–7.09 (m, 15H), 6.87 (d, J=8.1 Hz, 2H), 6.41 (d, J=15.7 Hz, 1H), 4.86 (s, 2H), 2.37 (q, J=7.3 Hz, 2H), 0.83 (t, J=7.3 Hz, 3H); APcI m/z: 576 (M+H$^+$).

Example LX

Preparation of 4-{3-[4-(1,2-diphenyl-but-1-enyl)-phenyl]-acryloylsulfamoyl}-N-methyl-benzamide

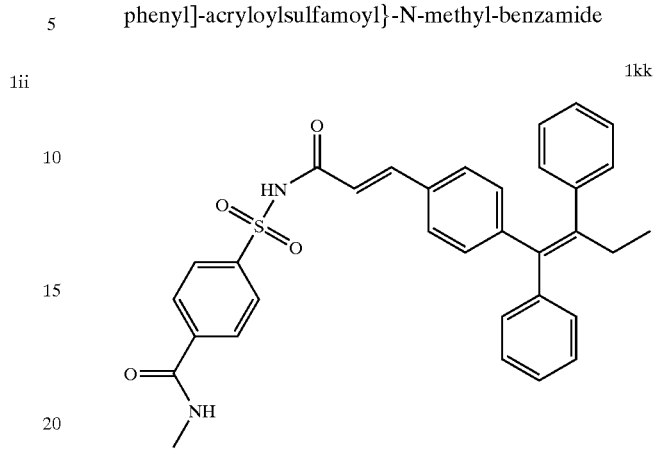

Example 1kk

Prepared from the coupling of 1ff and methylamine hydrochloride (2.5 eq) in the presence of BOP reagent (2.2 eq) and 4-methylmorpholine (1.5 eq) using N,N-dimethylformamide as solvent. Yield (32%); $^1$H NMR ($d_6$-DMSO) δ 13.48 (br s, 1H), 8.63 (q, J=4.4 Hz, 1H), 7.96 (s, 4H), 7.37–7.07 (m, 13H), 6.84 (d, J=8.4 Hz, 2H), 6.40 (d, J=15.7 Hz, 1H), 2.75 (d, J=4.4 Hz, 3H), 2.35 (q, J=7.7 Hz, 2H), 0.84 (t, J=7.7 Hz, 3H); APcI m/z: 549 (M−H$^-$).

Example LXI

Preparation of benzothiazole-2-sulfonic acid {3-[4-(1,2-diphenyl-but-1-enyl)-phenyl]-acryloyl}-amide

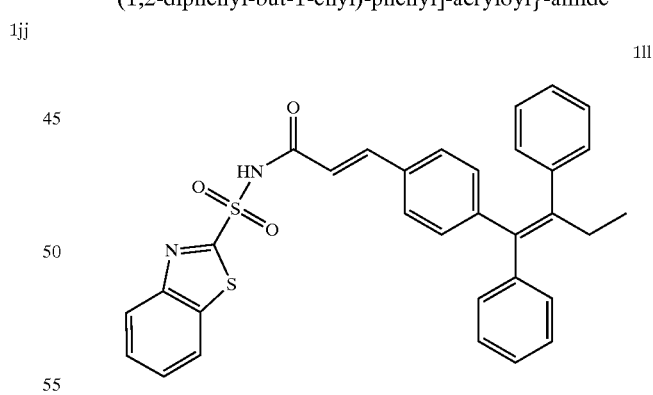

Example 1ll

Prepared from the coupling of 1a and 2-benzothiazolesulfonamide (J Org Chem, 1958, 1768) by the method described in Procedure 1, Method A. Yield (52%); $^1$H NMR ($d_6$-DMSO) δ 8.07 (d, J=8.3 Hz, 1H), 7.99 (d, J=8.3 Hz, 1H), 7.53–7.05 (m, 15H), 6.78 (d, J=8.1 Hz, 2H), 6.27 (d, J=15.7 Hz, 1H), 2.35 (q, J=7.3 Hz, 2H), 0.82 (t, J=7.3 Hz, 3H); APcI m/z: 551 (M+H$^+$).

Example LXII

Preparation of 3-chloro-propane-1-sulfonic acid {3-[4-(6-phenyl-8,9-dihydro-7H-benzocyclohepten-5-yl)-phenyl]-acryloyl}-amide

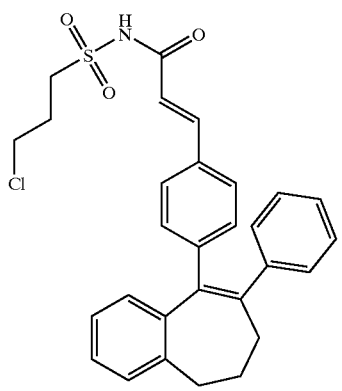

2i

Example 2i

Prepared from the coupling of 2e and 3-chloropropanesulfonamide by the method described in Procedure 1, Method A. Yield (65%); $^1$H NMR (d$_6$-DMSO) δ 11.83 (s, 1H), 7.54 (d, J=15.7 Hz, 1H), 7.34–7.09 (m, 10H), 6.87 (d, J=8.1 Hz, 2H), 6.70 (d, J=7.3 Hz, 1H), 6.51 (d, J=15.7 Hz, 1H), 3.72 (t, J=6.4 Hz, 2H), 3.54 (t, J=6.4 Hz, 2H), 2.77 (t, J=7.0 Hz, 2H), 2.26 (t, J=7.0 Hz, 2H), 2.08 (m, 4H); APcI m/z: 504 (M–H$^-$).

Example LXIII

Preparation of C,C,C-trifluoro-N-{3-[4-(6-phenyl-8,9-dihydro-7H-benzocyclohepten-5-yl)-phenyl]-acryloyl}-methanesulfonamide

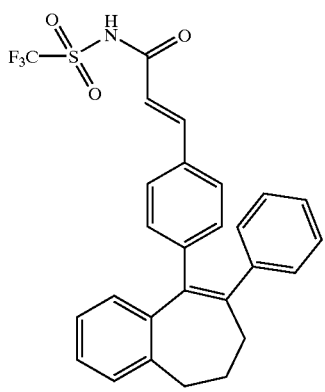

2j

Example 2j

Prepared from the coupling of 2e and trifluoromethanesulfonamide by the method described in Procedure 1, Method B. Yield (12%); $^1$H NMR (d$_6$-DMSO) δ 8.93 (br s, 2H), 7.31–7.07 (m, 9H), 6.80 (d, J=8.0 Hz, 2H), 6.72 (d, J=7.3 Hz, 1H), 6.35 (d, J=15.7 Hz, 1H), 2.76 (t, J=7.0 Hz, 2H), 2.26 (t, J=7.0 Hz, 2H), 2.07 (m, 2H); APcI m/z: 496 (M–H$^-$).

Example LXIV

Preparation of 3-piperidin-1-yl-propane-1-sulfonic acid {3-[4-(6-phenyl-8,9-dihydro-7H-benzocyclohepten-5-yl)-phenyl]-acryloyl}-amide

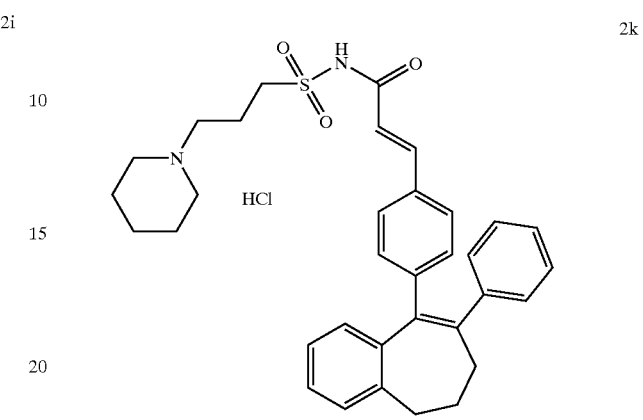

2k

Example 2k

Prepared from the coupling of 2i and piperidine (15 eq) in tetrahydrofuran at reflux. The product was isolated as the hydrochloride salt. Yield (70%); $^1$H NMR (d$_6$-DMSO) δ 11.90 (br s, 1H), 7.53 (d, J=15.7 Hz, 1H), 7.34–7.10 (m, 12H), 6.88 (d, J=8.4 Hz, 2H), 6.70 (d, J=7.3 Hz, 1H), 6.55 (d, J=15.7 Hz, 1H), 3.52 (t, J=7.3 Hz, 2H), 3.09 (br, 2H), 2.77 (br m, 4H), 2.26 (br t, 2H), 2.08 (br, 4H), 1.71 (br, 5H); APcI m/z: 555 (M+H$^+$).

Example LXV

Preparation of C-(4-fluoro-phenyl)-N-{3-[4-(6-phenyl-8,9-dihydro-7H-benzocyclohepten-5-yl)-phenyl]-acryloyl}-methanesulfonamide

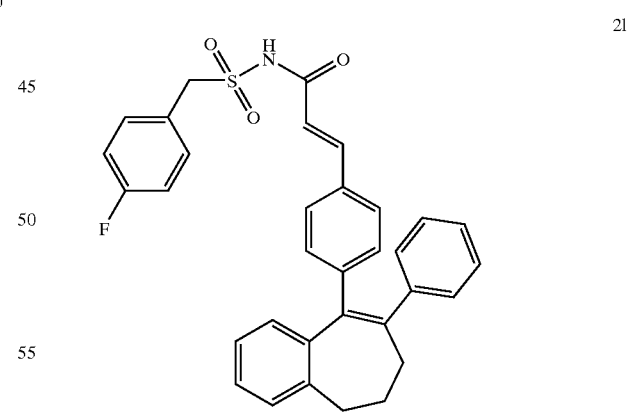

2l

Prepared from the coupling of 2e and 4-(fluorophenyl)methylsulfonamide (Synlett, 1997, 375) by the method described in Procedure 1, Method A. Yield (61%); $^1$H NMR (d$_6$-DMSO) δ 11.64 (br s, 1H), 7.58 (d, J=15.7 Hz, 1H), 7.33–7.11 (m, 14H), 6.88 (d, J=8.0 Hz, 2H), 6.70 (d, J=7.3 Hz, 1H), 6.45 (d, J=15.7 Hz, 1H), 4.72 (s, 2H), 2.77 (t, J=6.4 Hz, 2H), 2.26 (t, J=6.4 Hz, 2H), 2.08 (t, J=6.4 Hz, 2H); APcI m/z: 538 (M+H$^+$).

Example LXVI

Preparation of 4-(6-Methoxy-2-phenyl-1,2,3,4-tetrahydro-naphthalen-1-yl)-phenol

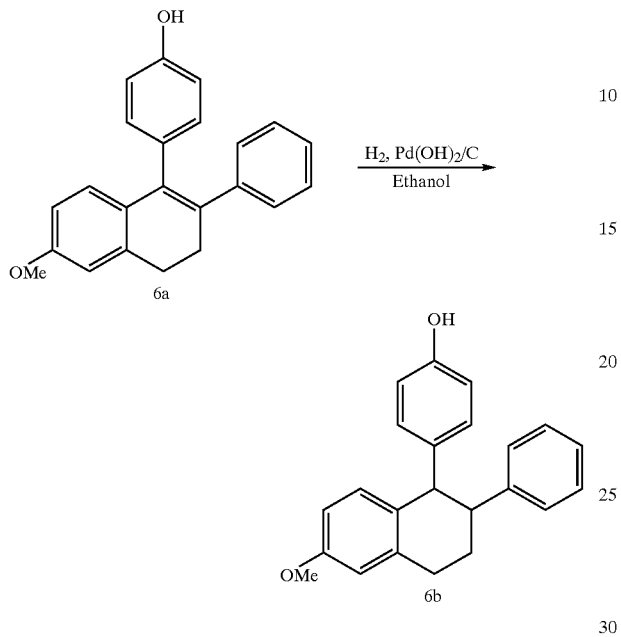

Compound 6a is prepared according to the method described on pages 172–176 of Volume 9 J. Med. Chem 1966. A suspension of 4-(4-hydroxyphenyl)-7-methoxy-3-phenyl-1,2-dihydronaphthalene 6a (829 mg, 2.52 mmol) and 20% Pd(OH)$_2$/C (500 mg) in ethanol (100 mL) was stirred 2 days under an atmosphere of hydrogen. The mixture was filtered through Celite and the solvent was removed under reduced pressure to give the cis-tetrahydronaphtahalene 6b as a white solid (834 mg, 100%): ESI m/z: 329 (M−H$^-$).

Example LXVII

Preparation of Trifluoro-methanesulfonic acid 4-(6-methoxy-2-phenyl-1,2,3,4-tetrahydro-naphthalen-1-yl)-phenyl ester

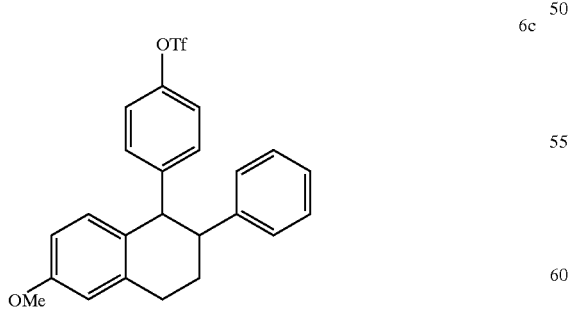

Prepared from the tetrahydronaphtahalene 6b by the general method described for example 3b. Yield (81%); $^{19}$F NMR (CDCl$_3$) δ−73.21.

Example LXVIII

Preparation of 3-[4-(6-Methoxy-2-phenyl-1,2,3,4-tetrahydro-naphthalen-1-yl)-phenyl]-acrylic acid methyl ester

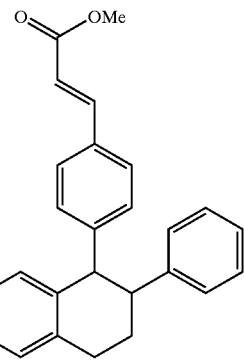

Prepared from the Heck coupling of 6c and methyl acrylate by the general method described for example 2b. Yield (83%); APcI m/z: 440 (M+H+CH$_3$CN$^+$, 100%).

Example LXX

Preparation of 3-[4-(6-Methoxy-2-phenyl-1,2,3,4-tetrahydro-naphthalen-1-yl)-phenyl]-acrylic acid

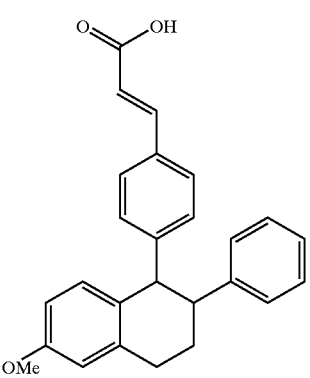

Prepared from the saponification (hydrolysis) of ester 6d by the general method described for example 2e. Yield (93%); APcI m/z: 426 (M+H+CH$_3$CN$^+$, 100%).

Example LXIX

Preparation of 3-[4-(6-Hydroxy-2-phenyl-1,2,3,4-tetrahydro-naphthalen-lyl)-phenyl]-acrylic acid

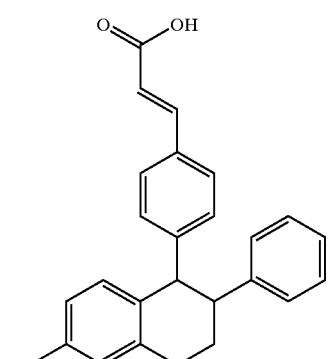

To a solution of the ether 6e (120 mg, 0.312 mmol) in CH$_2$Cl$_2$ (12 mL) at 0° C. was added 1M boron tribromide in CH$_2$Cl$_2$ (4 mL). The mixture was stirred 1.5 h at room temperature and was quenched with ice/H$_2$O. After stirring 2 h, the mixture was extracted with CH$_2$Cl$_2$. The combined organic layers were washed with water and dried (MgSO$_4$). The solvent was removed under reduced pressure and the residue was chromatographed (silica gel, 10–20% methanol/CH$_2$Cl$_2$) to give the phenol 6f as a white solid (45 mg, 39%): ESI m/z: 369 (M–H$^-$, 100%).

Example LXXI

Resolution of 3-[4-(6-Hydroxy-2-phenyl-1,2,3,4-tetrahydro-naphthalen-1-yl)-phenyl]-acrylic acid

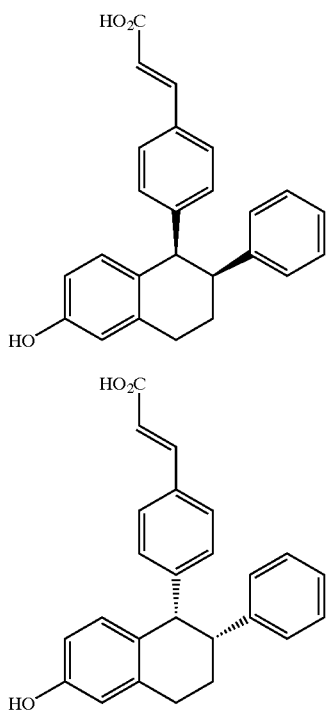

Resolution of 6f of Example LXX: The 2 enantiomers 6g and 6h were isolated by a preparative chiral HPLC of 6f. (Chiralcel OD column, trifluoroacetic acid/CH$_3$CN::1/1000 elutant).

Example LXXII

Preparation of Trifluoro-methanesulfonic acid 4-(2-phenyl-1,2,3,4-tetrahydro-naphthalen-1-yl)-phenyl ester

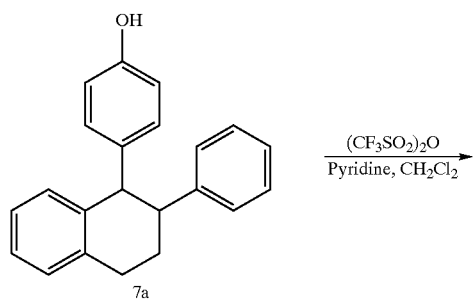

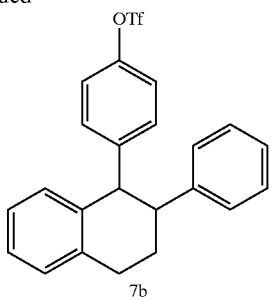

Compound 7a is prepared according to the procedure set forth on pages 138–144 of Volume 10 J. Med. Chem 1967. Compound 7b is then prepared from 4-(2-phenyl-1,2,3,4-tetrahydro-naphthalen-1-yl)-phenol (7a) by the general method described for example 3b. Yield (95%); $^1$H NMR (CDCl$_3$) δ 7.28–6.75 (m, 11H), 6.48 (d, J=8.4 Hz, 2H), 4.36 (d, J=5.4 Hz, 1H), 3.44 (m, 1H), 3.11 (m, 2H), 2.12 (m, 1H), 1.90 (m, 1H).

Example LXXIII

Preparation of 3-[4-(2-Phenyl-1,2,3,4-tetrahydro-naphthalen-1-yl)-phenyl]-acrylic acid methyl ester

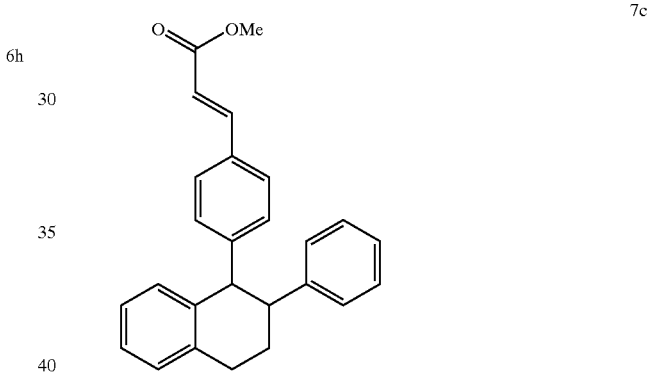

Prepared from the Heck coupling of 7b and methyl acrylate by the general method described for example 2b. Yield (76%); APcI m/z: 410 (M+H+CH$_3$CN$^+$, 100%).

Example LXXIV

Preparation of 3-[4-(2-Phenyl-1,2,3,4-tetrahydro-naphthalen-1-yl)-phenyl]-acrylic acid

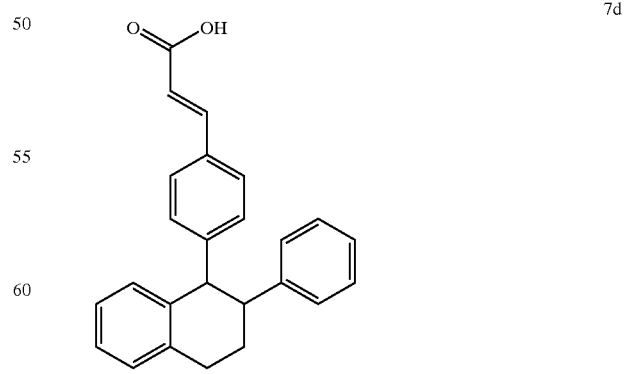

Prepared from the saponification (hydrolysis) of ester 7c by the general method described for example 2e. Yield (86%); ESI m/z: 353 (M–H$^-$, 100%).

Example LXXV

Preparation of N-{3-[4-(2-Phenyl-1,2,3,4-tetrahydro-naphthalen-1-yl)-phenyl]-acryloyl}-methanesulfonamide

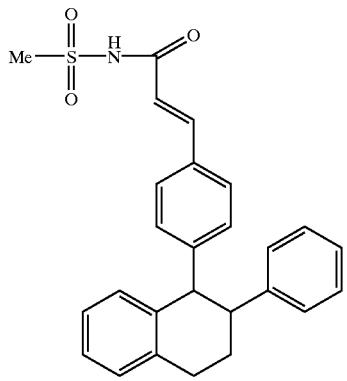

Prepared from the coupling of 7d and methylsulfonamide by the method described in Procedure 1, Method A. Yield (56%); $^1$H NMR (CDCl) δ 7.63 (d, J=15.4 Hz, 1H), 7.14 (m, 8H), 6.83 (m, 3H), 6.46 (d, J=8.1 Hz, 2H), 6.26 (d, J=15.4 Hz, 1H), 4.37 (d, J=5.1 Hz, 1H), 3.46 (m, 1H), 3.34 (s, 3H), 3.13 (m, 2H), 2.16 (m, 1H), 1.88 (m, 1H); ESI m/z: 430 (M−H⁻, 100%).

Example LXXVI

Preparation of N-{3-[4-(2-Phenyl-1,2,3,4-tetrahydro-naphthalen-1-yl)-phenyl]-acryloyl}-benzenesulfonamide

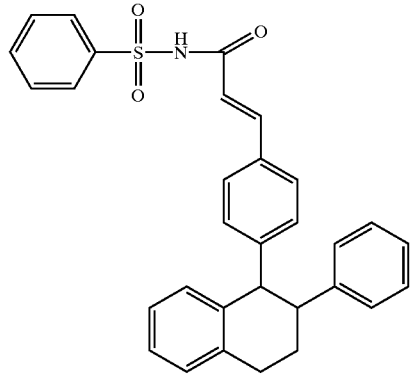

7f

Prepared from the coupling of 7d and benzene sulfonamide by the method described in Procedure 1, Method A. ESI m/z: 492 (M−H⁻, 100%).

Example LXXVII

Preparation of 4-(6-Phenyl-6,7,8,9-tetrahydro-5H-benzocyclohepen-5-yl)-phenol

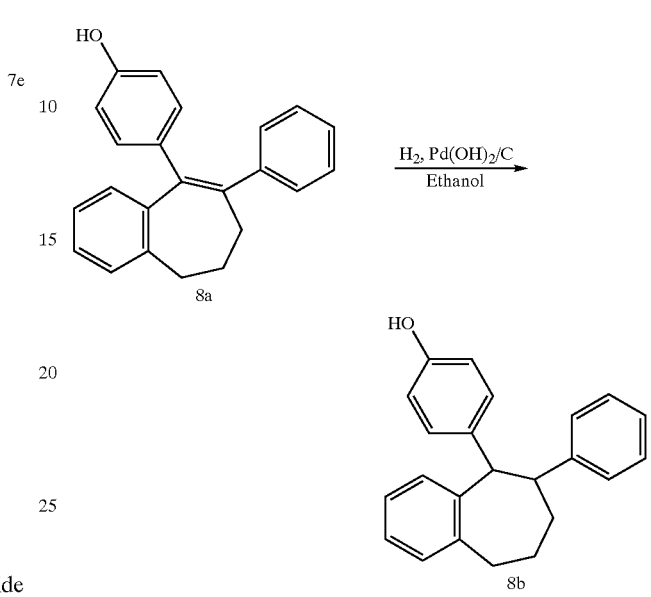

Compound 8a is prepared according to the synthesis shown at pages 2053–2059 of Volume 29 of the J. Med. Chem 1986. Prepared from 6,7-dihydro-8-phenyl-9-(4-hydroxyphenyl)-5H-benzocycloheptene (8a) by the general method described for example 6b. Yield (91%); $^1$H NMR (CDCl$_3$) δ 7.29–6.98 (m, 9H), 6.63 (m, 4H), 4.63 (d, J=1.5 Hz, 1H), 3.49 (m, 1H), 3.00 (m, 2H), 2.07 (m, 3H), 1.75 (m, 1H).

Example LXXVIII

Preparation of Triflouro-methanesulfonic acid 4-(6-phenyl-6,7,8,9-tetrahydro-5H-benzocyclohepten-5-yl)-phenyl ester

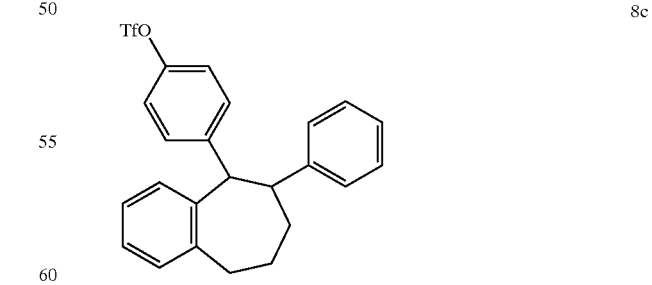

Prepared from 8b by the general method described for example 3b. Yield (89%); $^1$H NMR (CDCl$_3$) δ 7.31–6.84 (m, 13H), 4.70 (br s, 1H), 3.53 (br d, J=9.5 Hz, 1H), 2.98 (m, 2H), 2.17 (m, 1H), 2.00 (m, 2H), 1.75 (m, 1H).

Example LXXIX

Preparation of 3-[4-{6-Phenyl-6,7,8,9-tetrahydro-5H-benzocyclohepten-5-yl)-phenyl]-acrylic acid methyl ester Prepared from the Heck coupling of 8c and methyl acrylate by the general method described for example 2b. Yield (14%); APcI m/z: 424 (M+H+CH$_3$CN$^+$, 100%).

Example LXXX

Preparation of 3-[4-{6-Phenyl-6,7,8,9-tetrahydro-5H-benzocyclo hepten-5-yl)-phenyl]-acrylic acid Prepared from the saponification (hydrolysis) of ester 8d by the general method described for example 2e. Yield (30%); ESI m/z: 367 (M−H$^-$, 100%).

All aforementioned patent applications, patents and other publications are herein incorporated by reference in their entirety as though set forth in full.

What is claimed is:

1. A compound of Formula (I):

(I)

or pharmaceutically acceptable salt form thereof, wherein R$^1$ is

R$^2$ is selected from the group consisting of H, C$_{1-8}$ alkyl and halo;

R$^3$ is selected from the group consisting of H, C$_{1-8}$ alkyl, halo, and CN;

alternatively R$^2$ and R$^3$, together with the atoms to which they are attached, form a six- or seven-membered ring structure where one or more of the atoms forming the ring may be oxygen;

R$^4$ is selected from the group consisting of H, OH, C$_{1-8}$ alkyl, OC$_{1-8}$ alkyl and halo;

R$^5$ is selected from the group consisting of H, OH, CN, nitro, C$_{1-8}$ alkyl, OC$_{1-8}$ alkyl and halo;

R$^8$ is selected from the group consisting of aryl, C$_{1-8}$ alkyl, OH, and OC$_{1-8}$ alkyl, wherein said R$^8$ is optionally substituted with 1 to 2 substituents selected from halo, nitro, OH, CN, C$_{1-4}$ alkyl, OC$_{1-4}$ alkyl, NH$_2$, and NHC(O)OC(CH$_3$)$_3$; and the bond represented by a broken line and a solid line is an optional double bond.

2. A compound according to claim 1 wherein R$^2$ and R$^3$ together with the atoms to which they are attached form a seven-membered ring.

3. A compound according to claim 1 wherein R$^2$ and R$^3$ together with the atoms to which they are attached form a six membered ring.

4. A compound according to claim 1 wherein R$^3$ is CH$_3$.

5. A compound according to claim 1 wherein R$^3$ is CN.

6. A compound according to claim 1 wherein R$^2$ is H.

7. A compound according to claim 1 selected from the group consisting of:

v) N-{3-[4-(1,2-Diphenyl-but-1-enyl)-phenyl]-acryloyl}-methanesulfonamide;

w) N-{3-[4-(1,2-Diphenyl-but-1-enyl)-phenyl]-acryloyl}-benzenesulfonamide;

x) N-{3-[4-(1,2-Diphenyl-but-1-enyl)-phenyl]-acryloyl}phenyl-methanesulfonamide;

y) N-{3-[4-(1,2-Diphenyl-but-1-enyl)-phenyl]-acryloyl}-3-nitro-benzenesulfonamide;

z) N-{3-[4-(1,2-Diphenyl-but-1-enyl)-phenyl]-acryloyl-4-nitro-benzenesulfonamide;

aa) N-{3-[4-(1,2-Diphenyl-but-1-enyl)-phenyl]-acryloyl}-2-methyl-benzenesulfonamide;
ab) N-{3-[4-(1,2-Diphenyl-but-1-enyl)-phenyl]-acryloyl}-4-methyl-benzenesulonamide;
ac) N-{3-[4-(1,2-Diphenyl-but-1-enyl)-phenyl]-acryloyl}-2-nitro-benzenesulfonamide;
ad) N-{3-[4-(1,2-Diphenyl-but-1-enyl)-phenyl]-acryloyl}trifluoro-methanesulfonamide;
ae) N-{3-[4-(1,2-Diphenyl-but-1-enyl)-phenyl]-acryloyl}-4-methoxy-benzenesulfonamide;
af) 4-Chloro-N-{3-[4-(1,2-diphenyl-but-1-enyl)-phenyl]-acryloyl}-benzenesulfonamide;
ag) 4-Cyano-N-{3-[4-(1,2-diphenyl-but-1-enyl)-phenyl]-acryloyl}-benzenesulfonamide;
ah) N-{3-[4-(1,2-Diphenyl-but-1-enyl)-phenyl]-acryloyl}-3-trifluoromethyl-benzenesulfonamide;
ai) 2-Chloro-N-{3-[4-(1,2-diphenyl-but-1-enyl)-phenyl]-acryloyl}-benzenesulfonamide;
aj) 3-Chloro-N-{3-[4-(1,2-diphenyl-but-1-enyl)-phenyl]-acryloyl}-benzenesulfonamide;
ak) N-{3-[4-(2-Phenyl-3,4-dihydro-naphthalen-1-yl)-phenyl]-acryloyl}-methanesulfonamide;
al) N-{3-[4-(2-Phenyl-3,4-dihydro-naphthalen-1-yl)-phenyl]-acryloyl}-benzenesulfonamide;
am) N-{3-[4-(3-Phenyl-2H-chromen-4-yl)-phenyl]-acryloyl}-methanesulfonamide;
an) N-{3-[4-(3-Phenyl-2H-chromen-4-yl)-phenyl]-acryloyl}-benzenesulfonamide;
ap) N-{3-[4-(1,2-Diphenyl-but-1-enyl)-phenyl]-acryloyl}-2-trifluoromethyl-benzenesulfonamide;
aq) N-{3-[4-(1,2-Diphenyl-but-1-enyl)-phenyl]-acryloyl}-3-methyl-benzenesulfonamide;
ar) N-{3-[4-(1,2-Diphenyl-but-1-enyl)-phenyl]-acryloyl}-4-hydroxy-benzenesulfonamide;
as) N-{3-[4-(1,2-Diphenyl-but-1-enyl)-phenyl]-acryloyl}-3-methoxy-benzenesulfonamide;
at) N-{3-[4-(1,2-Diphenyl-but-1-enyl)-phenyl]-acryloyl}-4-trifluoromethyl-benzenesulfonamide;
au) N-{3-(4-(1,2-Diphenyl-but-1-enyl)-phenyl]-acryloyl}-3-hydroxy-benzenesulfonamide;
aw) N-{3-[4-(6-Phenyl-8,9-dihydro-7H-benzocyclohepten-5-yl)-phenyl]-acryloyl}-methanesulfonamide;
ax) N-{3-[4-(6-Phenyl-8,9-dihydro-7H-benzocyclohepten-5-yl)-phenyl]-acryloyl}-benzenesulfonamide;
ay) Phenyl-N-(3-[4-(2-phenyl-3,4-dihydro-naphthalen-1-yl)-phenyl]-acryloyl}-methanesulfonamide;
az) Phenyl-N-{3-[4-(6-phenyl-8,9-dihydro-7H-benzocyclohepten-5-yl)-phenyl]-acryloyl}-methanesulfonamide;
ba) 3-Chloro-propane-1-sulfonic acid {3-[4-(1,2-diphenyl-but-1-enyl)-phenyl]-acryloyl}-amide;
bb) (4-{3-[4-(1,2-Diphenyl-but-1-enyl)-phenyl]-acryloylsulfamoyl)-phenyl)-carbamic acid tert-butyl ester;
bd) 4-Amino-N-{3-[4-(1,2-diphenyl-but-1-enyl)-phenyl]-acryloyl}-benzenesulfonamide;
be) Ethanesulfonic acid {3-[4-(1,2-diphenyl-but-1-enyl)-phenyl]-acryloyl}-amide;
bg) Propane-2-sulfonic acid {3-[4-(1,2-diphenyl-but-1-enyl)-phenyl]-acryloyl}-amide;
bh) N-{3-[4-(1,2-Diphenyl-but-1-enyl)-phenyl]-acryloyl}-(4-fluoro-phenyl)-methanesulfonamide;
bi) 4-{3-[4-(1,2-Diphenyl-but-1-enyl)-phenyl]-acryloylsulfamoyl}-benzoic acid;
bk) 2,2,2-Trifluoro-ethanesulfonic acid {3-[4-(1,2-diphenyl-but-1-enyl)-phenyl]-acryloyl}-amide;
bl) 3-Chloro-propane-1-sulfonic acid {3-[4-(6-phenyl-8,9-dihydro-7H-benzocyclohepten-5-yl)-phenyl]-acryloyl}-amide;
bm) Trifluoro-N-{3-[4-(6-phenyl-8,9-dihydro-7H-benzocyclohepten-5-yl)-phenyl]-acryloyl}-methanesulfonamide;
bq) (4-Fluoro-phenyl)-N-{3-[4-(6-phenyl-8,9-dihydro-7H-benzocyclohepten-5-yl)-phenyl]-acryloyl}-methanesulfonamide; and
bs) N-{3-[4-(1,2-Diphenyl-but-1-enyl)-phenyl]-acryloyl}(4-trifluoromethyl-phenyl)-methanesulfonamide.

8. A pharmaceutical composition comprising a pharmaceutically acceptable carrier in combination with a therapeutically effective amount of a compound of claim 1.

9. A method of treating breast, uterine, ovarian, prostate or colon cancer, osteoporosis, endometriosis, uterine fibroid, Alzheimer's disease, macular degeneration, urinary incontinence or type II diabetes, comprising: administering to a host in need of such treatment a therapeutically effective amount of a compound of claim 1.

* * * * *

UNITED STATES PATENT AND TRADEMARK OFFICE
CERTIFICATE OF CORRECTION

PATENT NO. : 6,927,224 B2
DATED : August 9, 2005
INVENTOR(S) : Kaltenbach et al.

It is certified that error appears in the above-identified patent and that said Letters Patent is hereby corrected as shown below:

Column 56,
Line 24, "Example LXX" should be replaced with -- Example LXIX --.
Line 47, "Example LXIX" should be replaced with -- Example LXX --.
Line 49, "tetrahydro-naphthalen-1yl)-phenyl]-acrylic acid" should be replaced with
-- tetrahydro-naphthalen-1-yl)-phenyl]-acrylic acid --.

Signed and Sealed this

Eighth Day of November, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,927,224 B2 | Page 1 of 1 |
| APPLICATION NO. | : 10/216253 | |
| DATED | : August 9, 2005 | |
| INVENTOR(S) | : Robert F. Kaltenbach, Simon P. Robinson and George L. Trainor | |

It is certified that error appears in the above-identified patent and that said Letters Patent is hereby corrected as shown below:

On the Title Page at section (73) Assignee, "Bristol Myers Squibb Company" should be replaced with --Bristol-Myers Squibb Pharma Company--.

Signed and Sealed this

Twelfth Day of June, 2007

JON W. DUDAS
*Director of the United States Patent and Trademark Office*